(12) United States Patent
Baker et al.

(10) Patent No.: US 11,694,576 B2
(45) Date of Patent: Jul. 4, 2023

(54) INJECTION SIMULATION DEVICE AND METHOD

(71) Applicant: NOBLE INTERNATIONAL, INC., Orlando, FL (US)

(72) Inventors: Jeff Baker, Orlando, FL (US); Christopher Wai Yin Chung, Orlando, FL (US); Tingting Liu, Orlando, FL (US); Shishuang Hou, Ningbo (CN); Dinesh Venkata Koka, Winter Park, FL (US)

(73) Assignee: NOBLE INTERNATIONAL, INC., Orlando, FL (US)

( * ) Notice: Subject to any disclaimer, the term of this patent is extended or adjusted under 35 U.S.C. 154(b) by 864 days.

(21) Appl. No.: 16/484,358

(22) PCT Filed: Feb. 7, 2018

(86) PCT No.: PCT/US2018/017300
§ 371 (c)(1),
(2) Date: Aug. 7, 2019

(87) PCT Pub. No.: WO2018/148337
PCT Pub. Date: Aug. 16, 2018

(65) Prior Publication Data
US 2020/0258424 A1 Aug. 13, 2020

Related U.S. Application Data

(60) Provisional application No. 62/455,934, filed on Feb. 7, 2017.

(51) Int. Cl.
*G09B 23/28* (2006.01)
*A61M 5/20* (2006.01)
(Continued)

(52) U.S. Cl.
CPC .............. *G09B 23/285* (2013.01); *A61M 5/20* (2013.01); *A61M 5/315* (2013.01); *A61M 5/326* (2013.01); *A61M 2005/3267* (2013.01)

(58) Field of Classification Search
CPC ....... G09B 23/285; A61M 5/20; A61M 5/315; A61M 5/326; A61M 2005/3267
(Continued)

(56) References Cited

U.S. PATENT DOCUMENTS 5,071,353 A 12/1991 Van Der Wal
7,901,377 B1 8/2011 Harrison et al.
(Continued)

FOREIGN PATENT DOCUMENTS

DE 102005062610 6/2007
DE 102005062611 6/2007
(Continued)

OTHER PUBLICATIONS

International Search Report and Written Opinion for PCT Application PCT/US16/014987 dated Nov. 14, 2016, pp. 1-13.
(Continued)

*Primary Examiner* — Robert P Bullington
(74) *Attorney, Agent, or Firm* — Timothy H. Van Dyke; Wolter, Van Dyke, Davis, PLLC

(57) ABSTRACT

In an embodiment provided herein, an injection simulation device including a housing having a proximal end and a distal end is provided. The injection simulation device embodiment comprises a plunger having a proximal end, a distal end and being slidable relative to the housing, and a retractable injection simulation member at the distal end of the housing, at least one biasing member associated with the retractable injection simulation member and associated with the plunger, wherein a first force on a distal end of the injection simulation member causes movement of the injec-
(Continued)

tion simulation member from an extended position to a retracted position, to compress the first biasing member, and simulate the tactility of an injection to a user; and wherein a second force on the proximal end of the plunger asserts a third force on the first biasing member to facilitate resetting the injection simulation member to the extended position.

13 Claims, 18 Drawing Sheets

(51) Int. Cl.
    *A61M 5/315*     (2006.01)
    *A61M 5/32*     (2006.01)

(58) Field of Classification Search
    USPC .......................................................... 434/262
    See application file for complete search history.

(56) References Cited

U.S. PATENT DOCUMENTS

| | | |
|---|---|---|
| 8,342,851 B1 | 1/2013 | Speeg et al. |
| 2006/0008786 A1 | 1/2006 | Feygin et al. |
| 2007/0111175 A1 | 5/2007 | Raven et al. |
| 2009/0305213 A1 | 12/2009 | Burgkart et al. |
| 2011/0144594 A1 | 6/2011 | Sund et al. |
| 2012/0015336 A1 | 1/2012 | Mach |
| 2012/0040320 A1 | 2/2012 | Nadeau |
| 2013/0236872 A1 | 9/2013 | Laurusonis et al. |
| 2015/0235571 A1* | 8/2015 | Alexandersson . A61M 5/31501 434/262 |
| 2016/0361503 A1* | 12/2016 | Bendek ................... A61M 5/24 |
| 2017/0004737 A1 | 1/2017 | Baker et al. |

FOREIGN PATENT DOCUMENTS

| | | |
|---|---|---|
| EP | 2784766 | 1/2014 |
| EP | 3335213 A1 | 6/2018 |
| WO | 2013130973 A1 | 9/2013 |
| WO | 2014/145535 | 9/2014 |
| WO | 2014/164948 | 10/2014 |
| WO | 2016/123144 | 8/2016 |
| WO | 2017/007850 | 1/2017 |
| WO | 2017027753 A1 | 2/2017 |

OTHER PUBLICATIONS

International Search Report and Written Opinion for PCT Application PCT/US18/17300 dated Aug. 24, 2018, pp. 1-7.
Extended European Search Report for EP Application P16743991.8, dated Jun. 20, 2018, pp. 1-8.
Nam, S. et al, (2010). Factors associated with psychological insulin resistance in individuals with Type 2 diabetes. Diabetes Care, 33, 1747-1749.
Noble, "Helix—Concept Refinement", InSight Presentation, pp. 1-7 (2016).
Noble, "Helix—Greaseless Damping Concepts", InSight Presentation, pp. 1-10 (2017).
Zambanini, A., et al, (1999). Injection related anxiety in insulin-treated diabetes. Diabetes Research and Clinical Practice, 46, 239-246.
EP16743991.8, Search Report, dated Jul. 21, 2020, 9 pages.
EESR; EP Application No. 18751302.3; Dec. 8, 2020, 7 pages.

\* cited by examiner

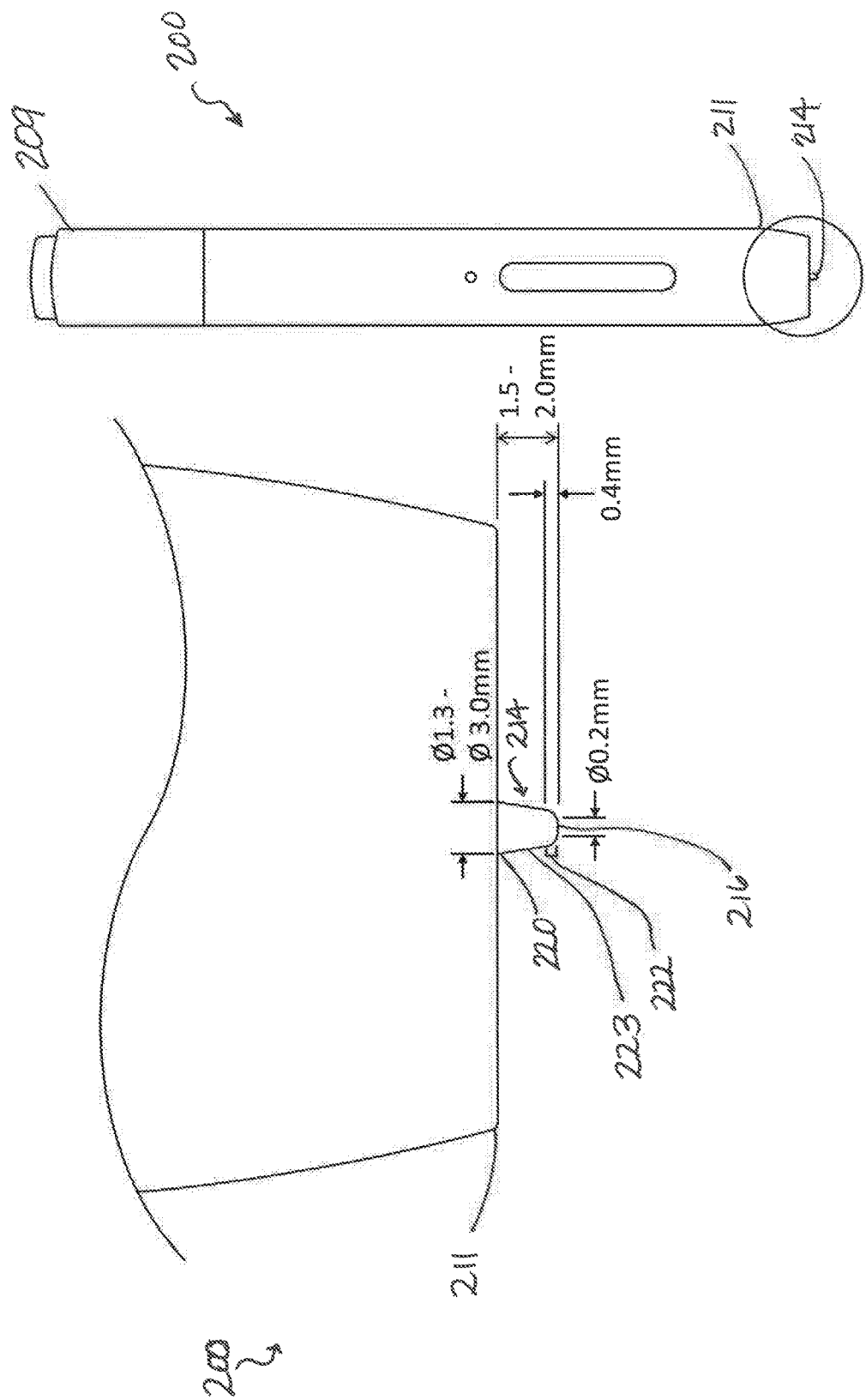

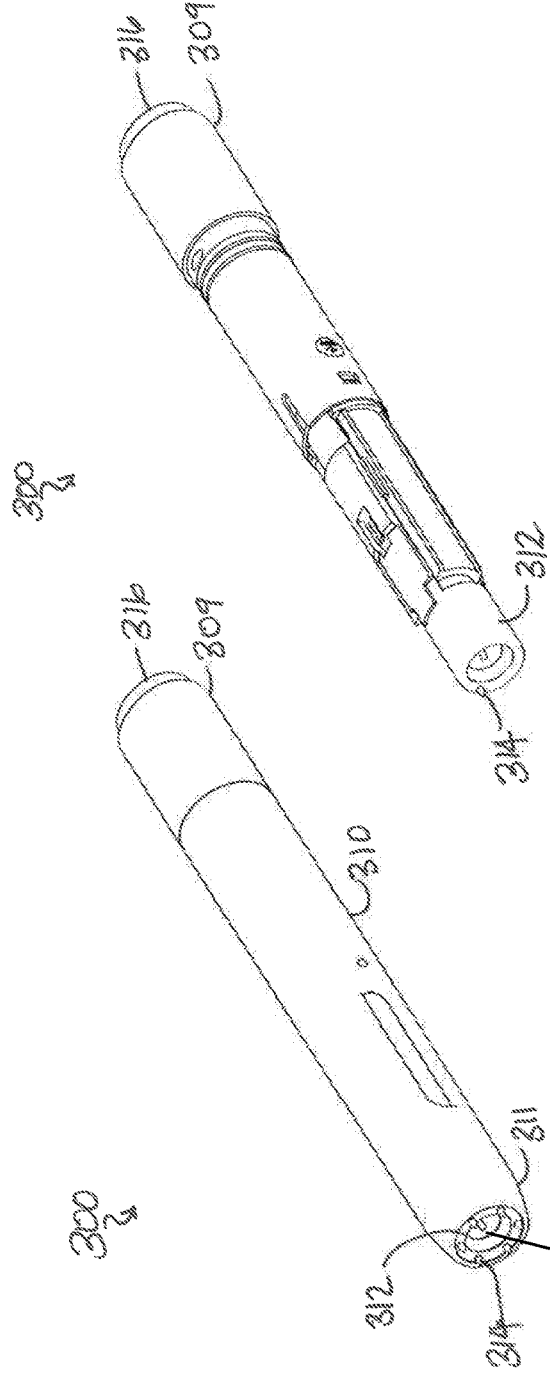

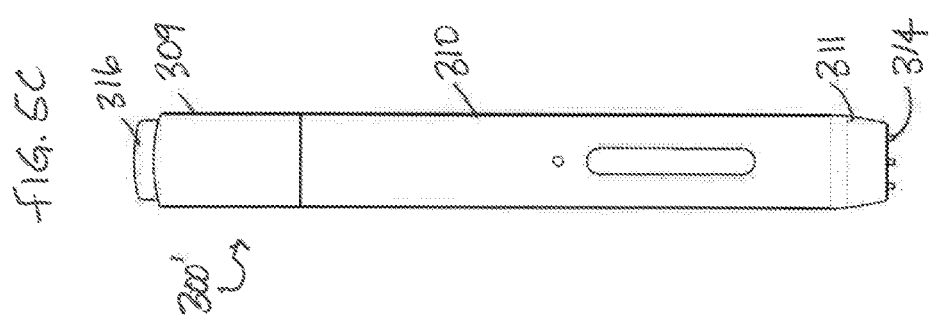
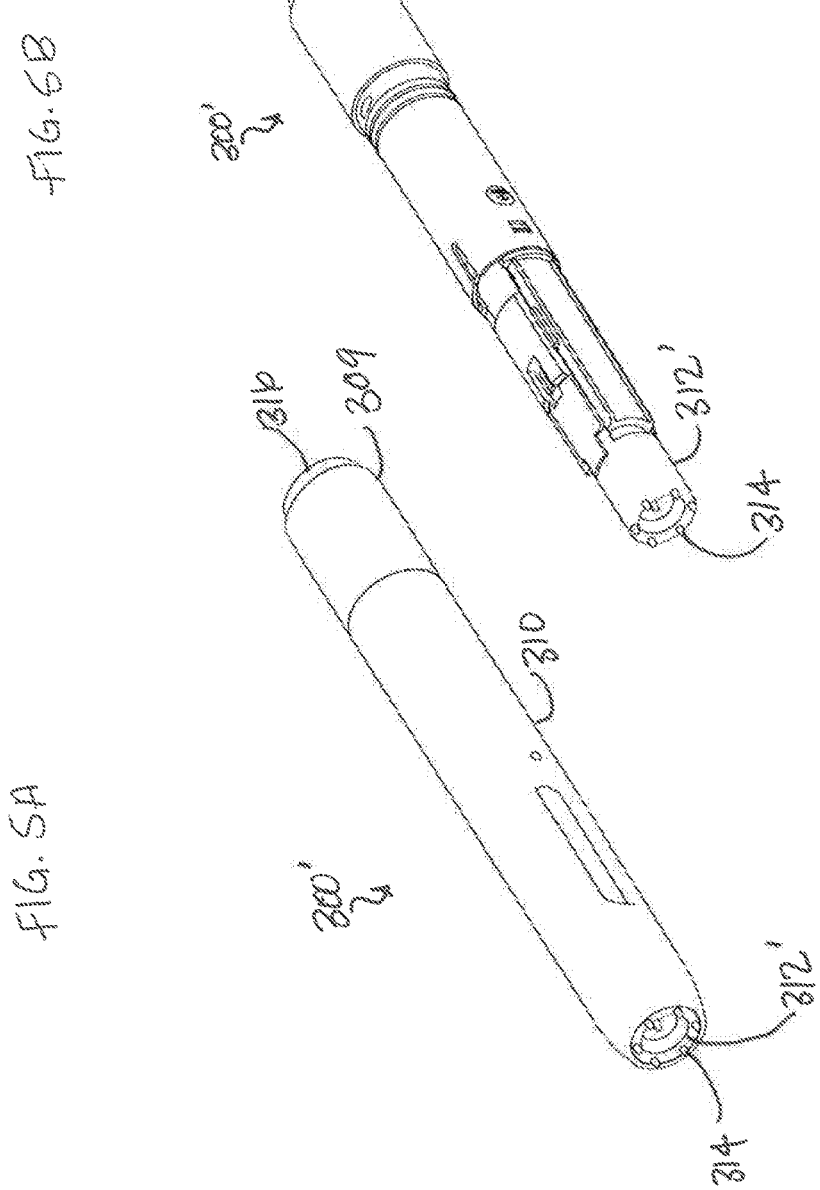

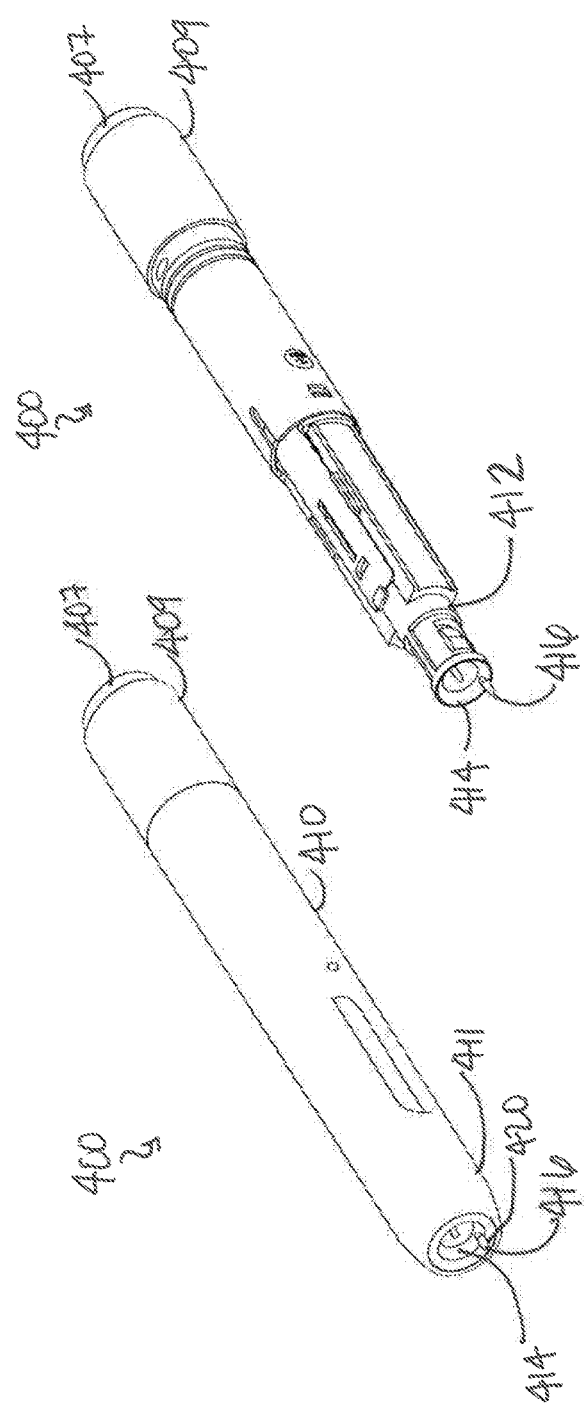

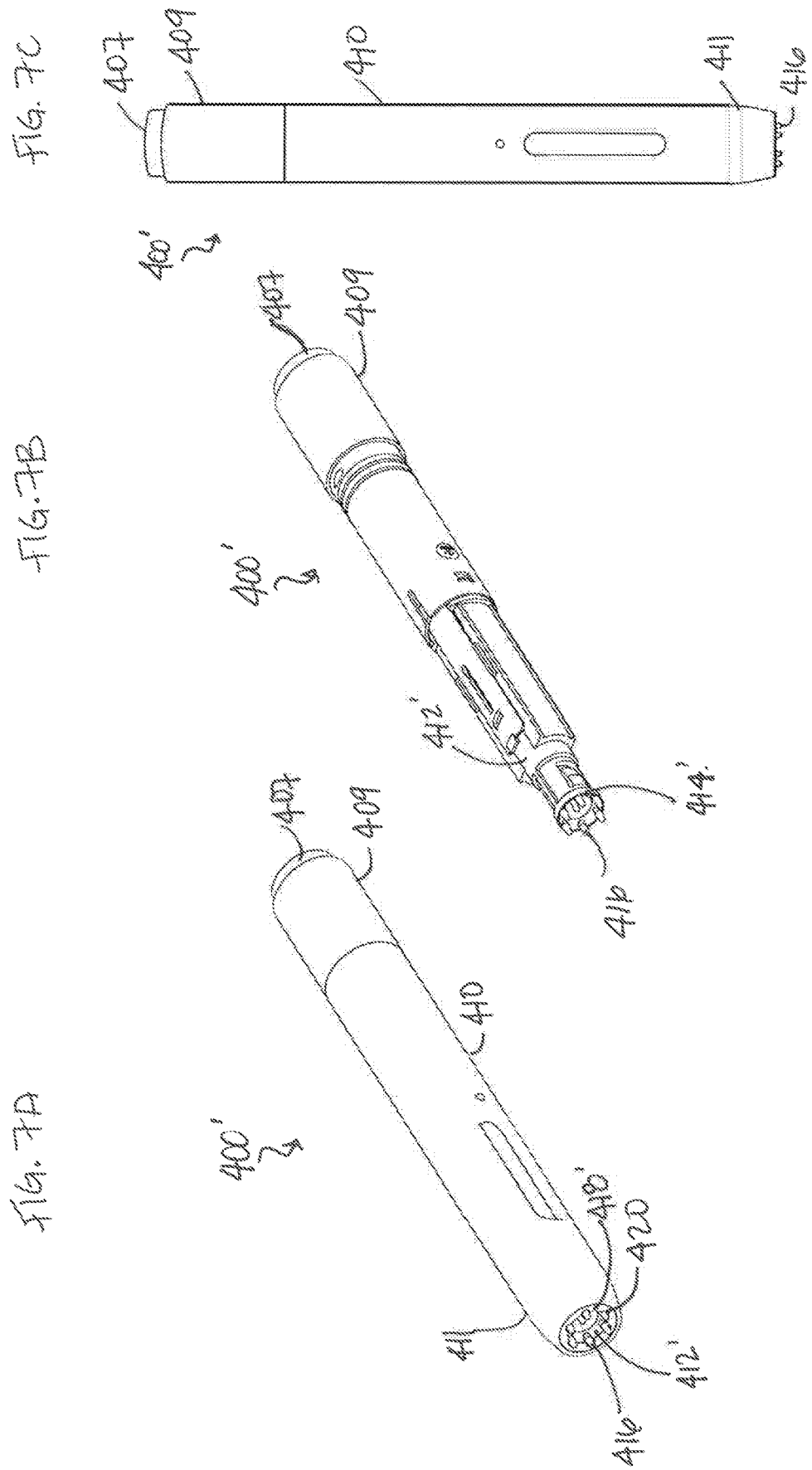

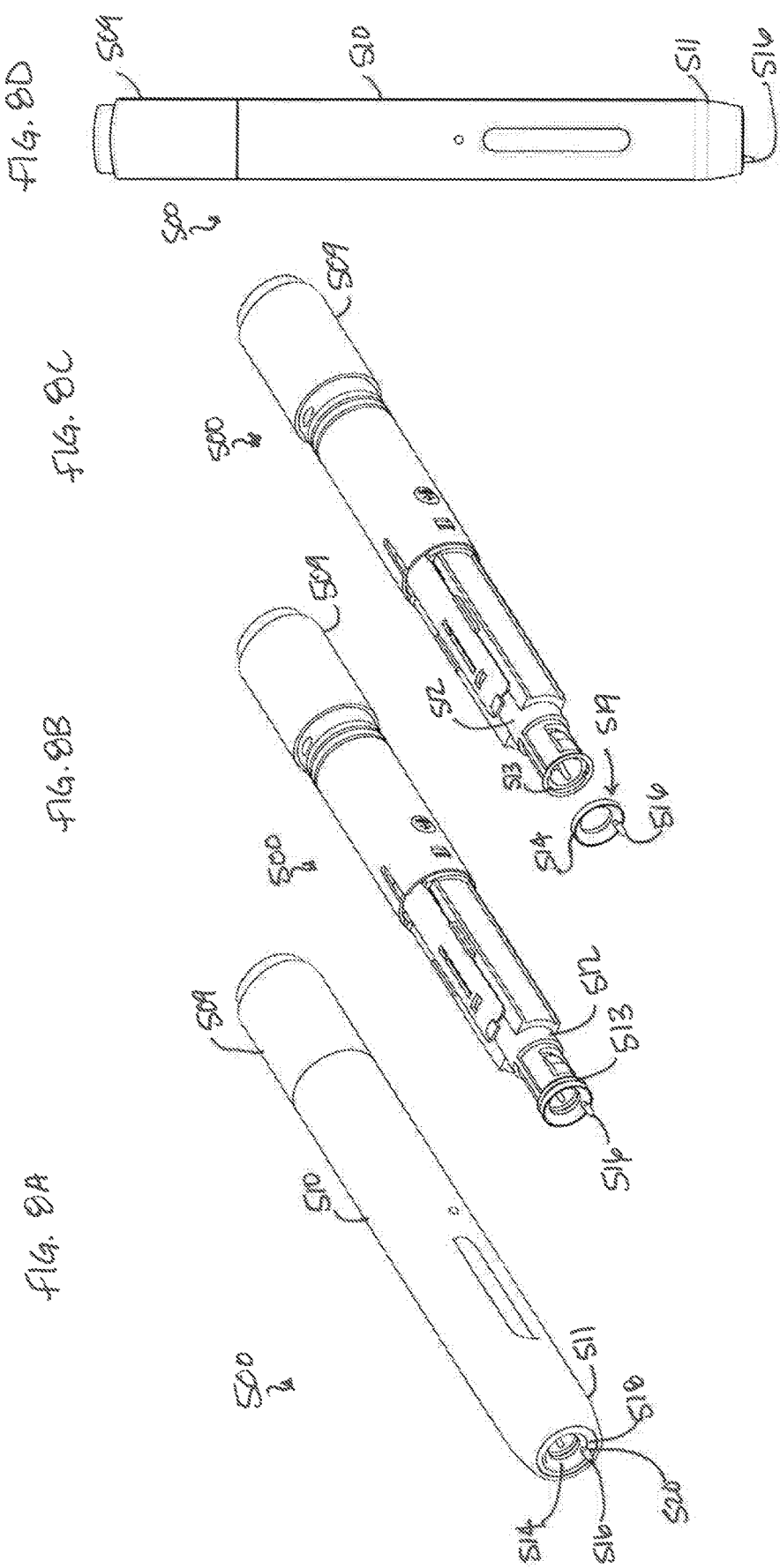

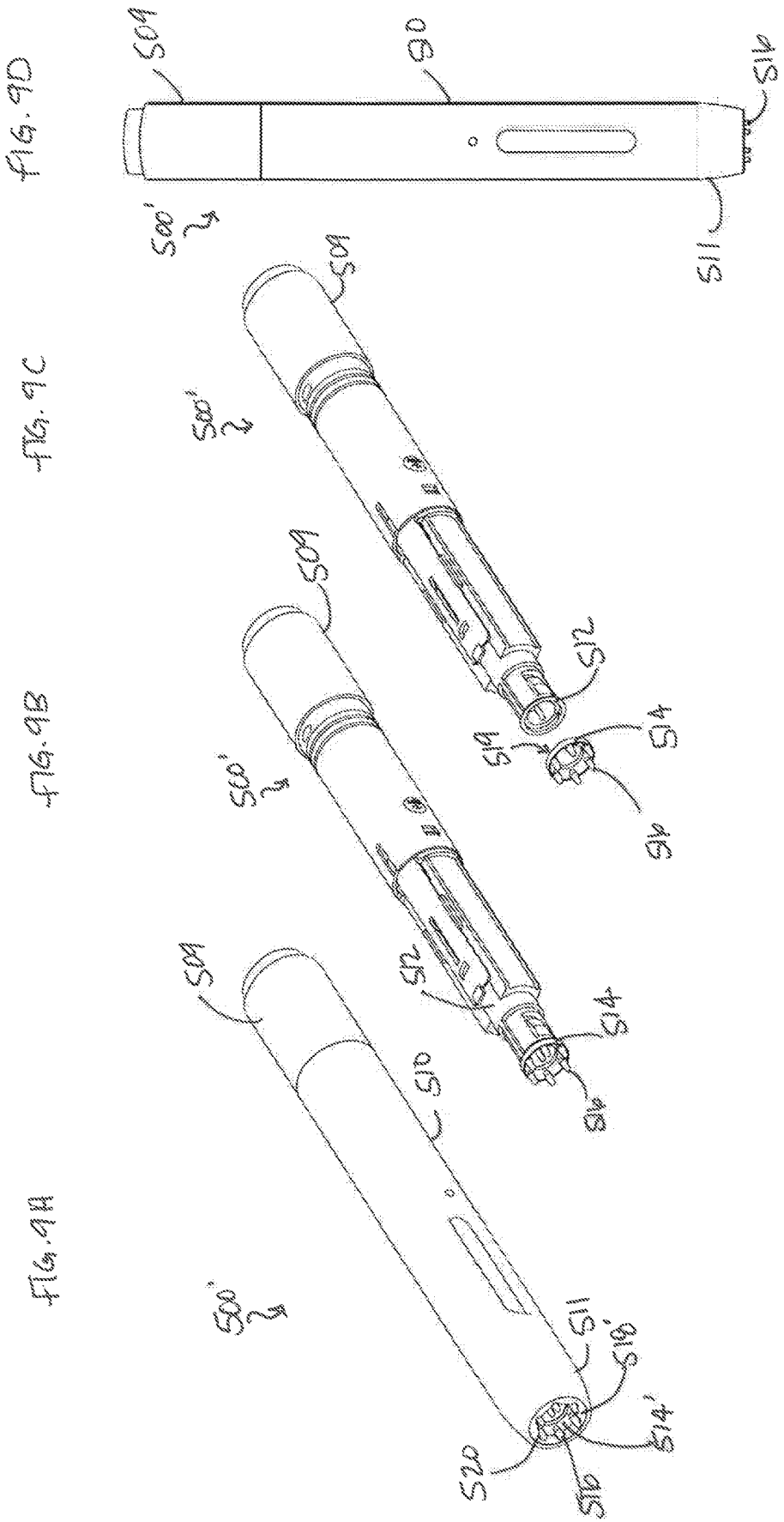

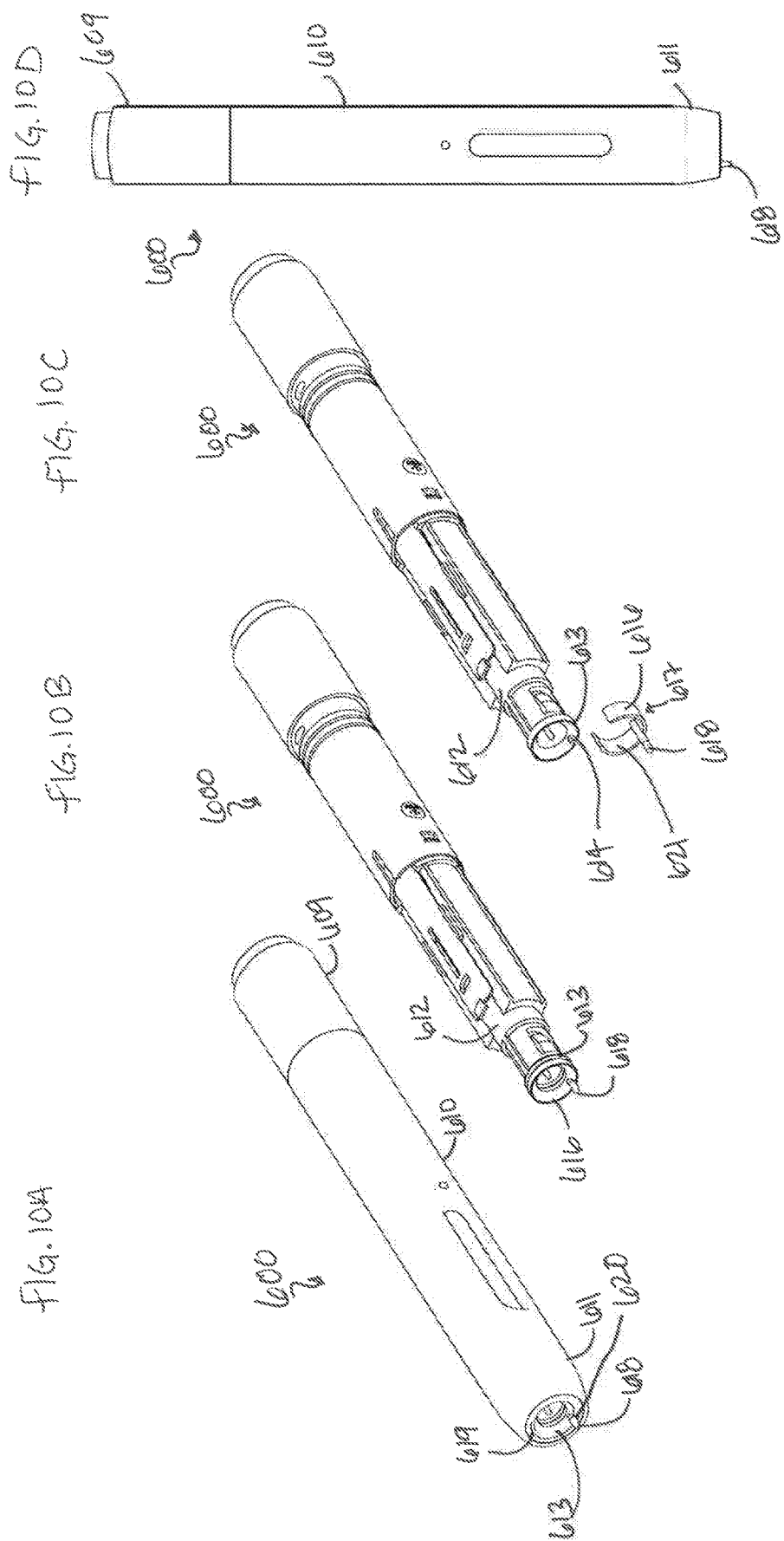

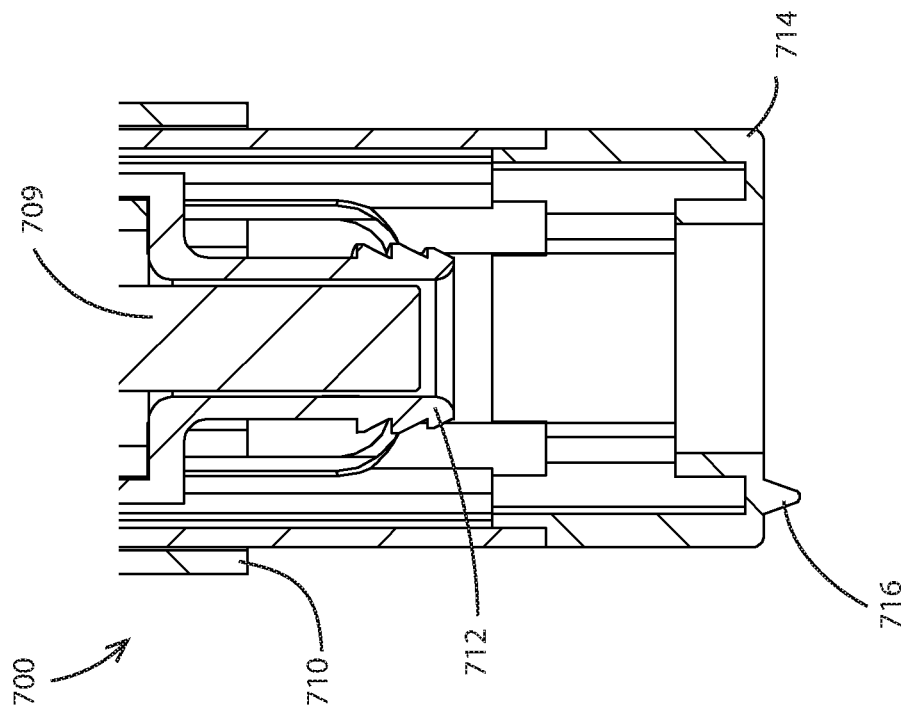
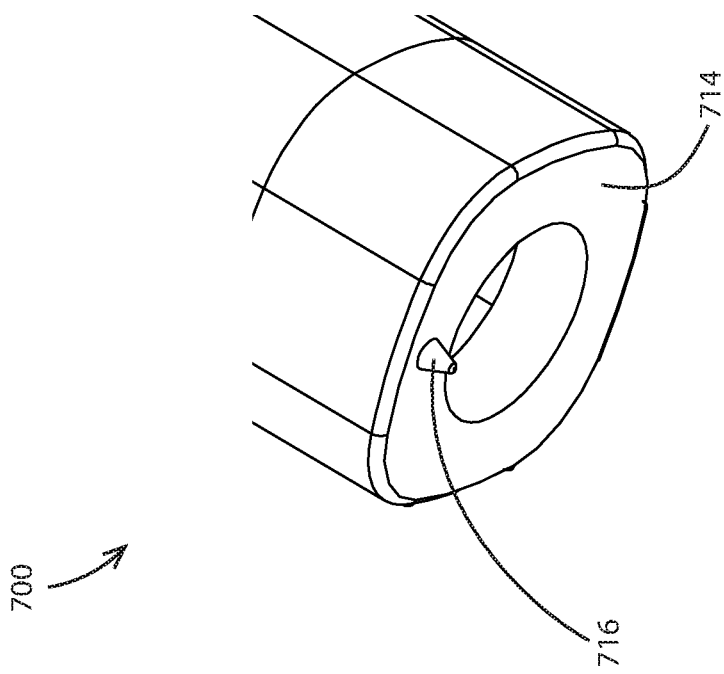
FIG.12B
FIG.12A

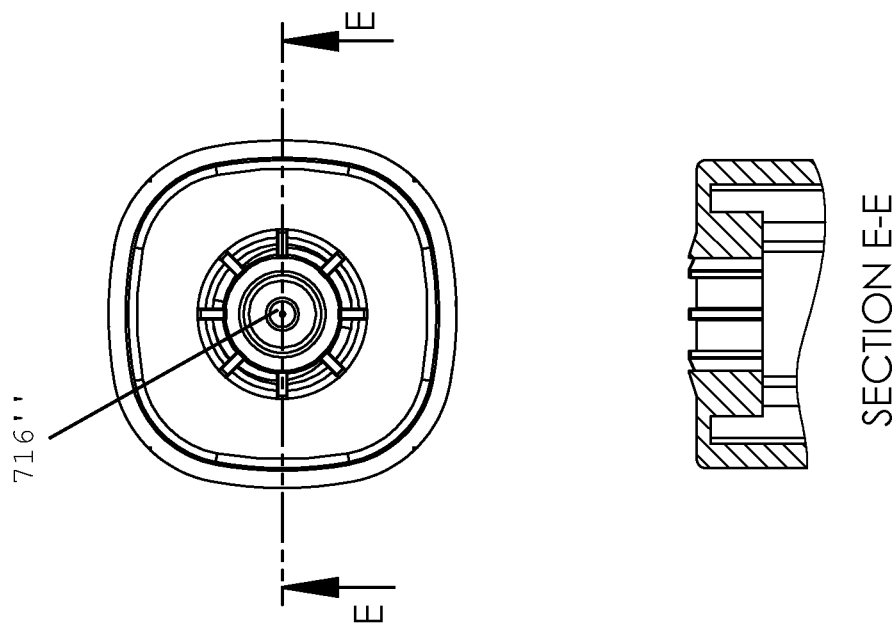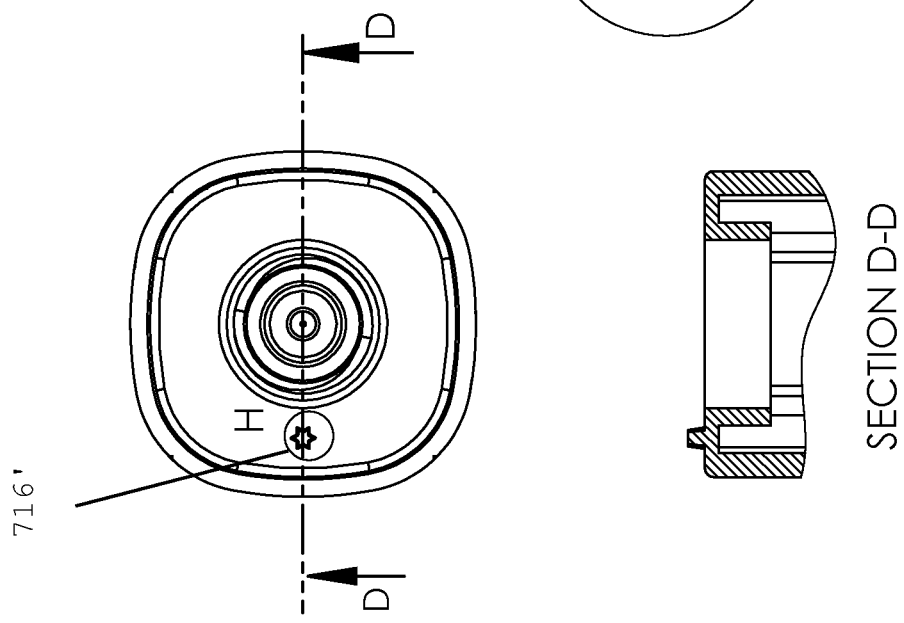

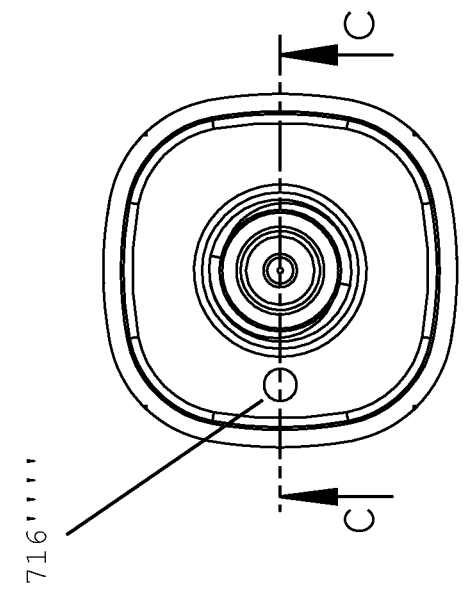
FIG.12F
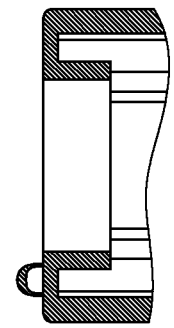
SECTION C-C
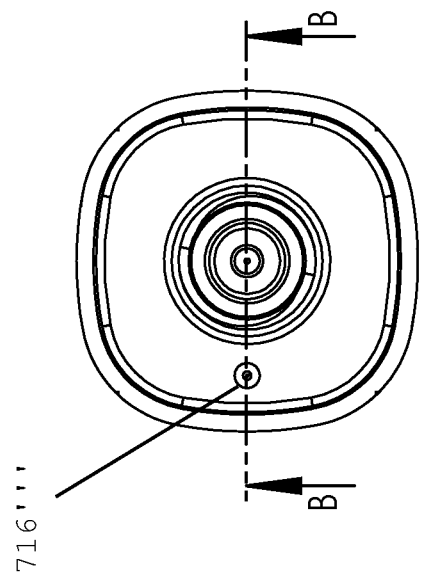
FIG.12E
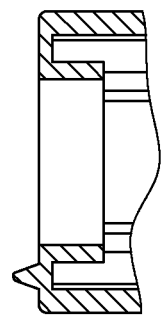
SECTION B-B

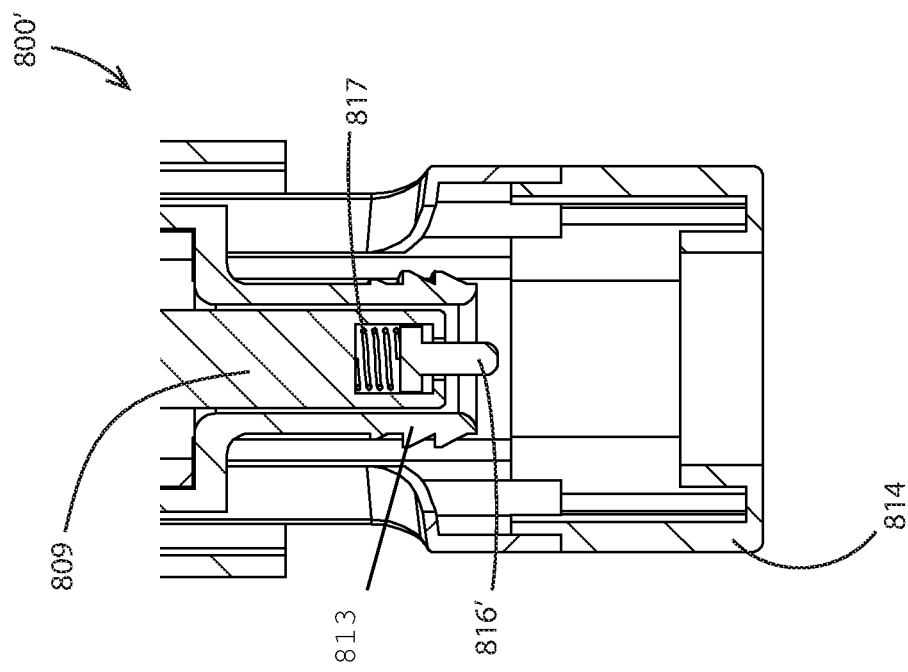
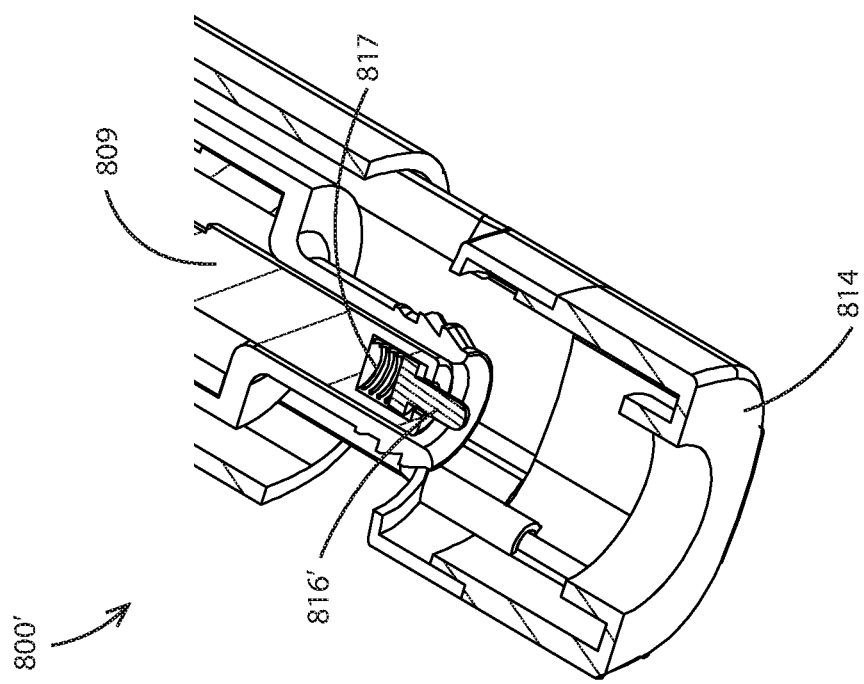

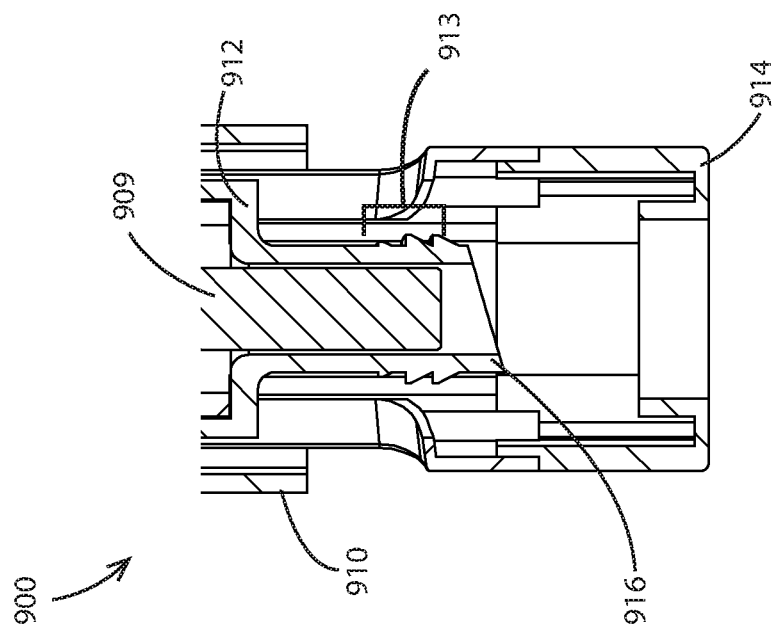
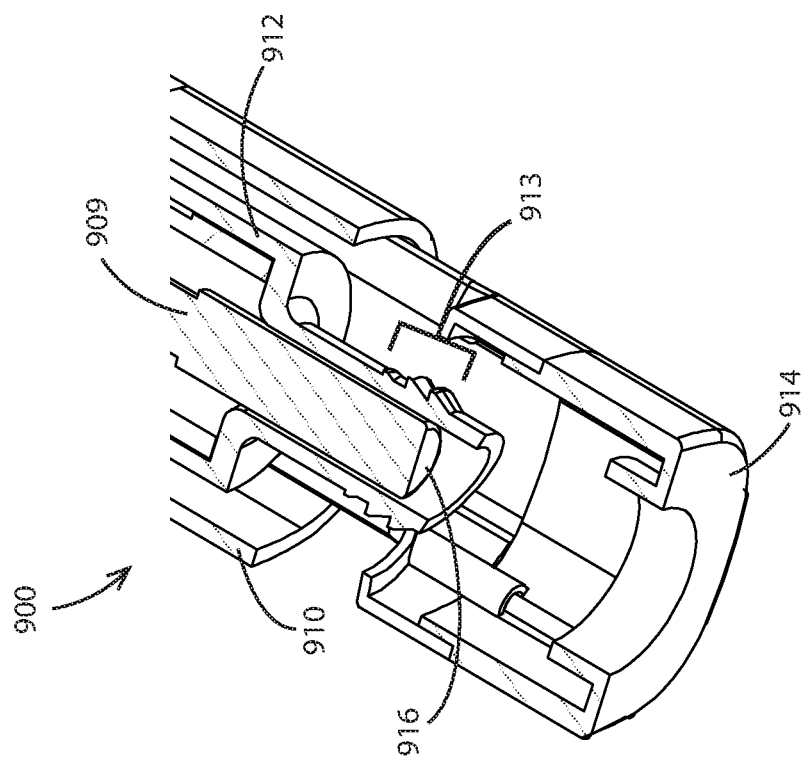

INJECTION SIMULATION DEVICE AND METHOD

CROSS REFERENCE TO RELATED APPLICATIONS

This application is related to U.S. Patent Application No. 62/455,934 filed on Feb. 7, 2017, which is incorporated by reference herein and to which priority is claimed.

BACKGROUND

The use of needles and instruments containing needles are widespread in the medical industry. Needle insertion into a patient is an essential component of many clinical procedures such as biopsies, injections, neurosurgery, and cancer treatment methods. The success of these procedures depends on accurate placement and insertion of the needle into a target region of a patient. Accuracy of an injection can be hampered by certain factors, including a fear of needles and/or injections leading to failure to administer an injection, or improper administration of an injection, and lack of knowledge and/or experience in administering injections to oneself or to others which may also lead to improper injection administration.

Increased use of biologic and large molecule drugs has driven the demand for prefilled syringes and other drug delivery systems. Prefilled syringes are combination products used in home and institutional settings by patients and health care providers (HCP). Failure to effectively use a prefilled syringe can result in errors that adversely affect the safe and full delivery of a prescribed dose. Training users of prefilled syringes and other drug delivery systems serves as an attractive strategy to mitigate errors and support the commercial objectives of syringe products and other medication administration products in the market.

Injectable medications are required for a number of varying illnesses and diseases. Many injectable medications require self-injection by a patient. Self-injection of a medicament using a device having a needle carries with it a certain stigma. Oftentimes users are weary of injecting the subject (whether it be themselves or another patient) with an injection device for fear or anxiety related to failing to deliver a complete dose of the medication, anticipated pain associated with injecting the subject with the needle, fear of accidentally sticking themselves with the needle during manipulation of the injection device, and difficulties in adequately grasping the dosing mechanism or injection device to inject the subject, among other concerns. An additional concern exists in instances in which users with little or no medical knowledge or experience are required to inject themselves or another subject using these devices. Performing a medical treatment or test using a device having or requiring a needle carries with it certain risks and often creates a level of anxiety for the user performing the treatment or test and/or for the subject receiving the treatment or test.

It has proven beneficial in the medical field to practice performing medical techniques prior to administering a medical treatment, particularly when it relates to medical treatments by way of injections or other invasive drug delivery means. The ability to practice delivering injections to oneself or to another prior to use of a drug delivery device, with a device that resembles the drug delivery device, is of significant benefit to the user.

SUMMARY

In an embodiment provided herein, an injection simulation device including a housing having a proximal end and a distal end is provided. The injection simulation device embodiment comprises a plunger having a proximal end and a distal end and being slidable relative to the housing, and a retractable injection simulation member at the distal end of the housing, the retractable injection simulation member being movable between an extended position and a retracted position, at least one first biasing member, wherein the at least one first biasing member is associated with the retractable injection simulation member, and directly or indirectly associated with the plunger, wherein a first force on a distal end of the injection simulation member causes movement of the injection simulation member from an extended position to a retracted position, to compress the first biasing member, and simulate the tactility of an injection to a user; and wherein a second force on the proximal end of the plunger asserts a third force directly or indirectly on the first biasing member to facilitate resetting the injection simulation member to the extended position.

In another embodiment, an injection simulation device comprising a proximal end and a distal end, and comprising at least one agitator configured to associate with the distal end of the device such that the agitator contacts a surface of a user to simulate the tactile feel of a needle during an injection without puncturing the surface is provided.

In yet another embodiment, a removable apparatus that associates with an injection simulation device including a device interfacing portion that secures the apparatus to the injection simulation device; and at least one agitator, wherein operation of the injection simulation device exposes the at least one agitator so as to interact with a surface of a user, the agitator configured to simulate the tactility of a needle without puncturing the surface is provided.

BRIEF DESCRIPTION OF THE DRAWINGS

A more particular description briefly stated above will be rendered by reference to specific embodiments thereof that are illustrated in the appended drawings. Understanding that these drawings depict only typical embodiments and are not therefore to be considered to be limiting of its scope, the embodiments will be described and explained with additional specificity and detail through the use of the accompanying drawings in which:

FIG. 3A is a side view of an autoinjector simulation embodiment.

FIG. 3B is a side view of a distal portion of an autoinjector simulation embodiment.

FIG. 4A is a perspective view of an autoinjector simulation embodiment having multiple agitators on a distal portion thereof.

FIG. 4B is a perspective, partial view of an autoinjector simulation embodiment having an agitator on a distal portion thereof.

FIG. 4C is a side view of an autoinjector simulation embodiment having an agitator on a distal portion thereof.

FIG. 5A is a perspective view of an autoinjector simulation embodiment having multiple agitators on a distal portion thereof.

FIG. 5B is a perspective, partial view of an autoinjector simulation embodiment having multiple agitators on a distal portion thereof.

FIG. 5C is a side view of an autoinjector simulation embodiment having multiple agitators on a distal portion thereof.

FIG. 6A is a perspective view of an autoinjector simulation embodiment having an agitator on a distal portion thereof.

FIG. 6B is a perspective, partial view of an autoinjector simulation embodiment having an agitator on a distal portion thereof.

FIG. 6C is a side view of an autoinjector simulation embodiment having an agitator on a distal portion thereof.

FIG. 7A is a perspective view of an autoinjector simulation embodiment having multiple agitators on a distal portion thereof.

FIG. 7B is a perspective, partial view of an autoinjector simulation embodiment having multiple agitators on a distal portion thereof.

FIG. 7C is a side view of an autoinjector simulation embodiment having multiple agitators on a distal portion thereof.

FIG. 8A is a perspective view of an autoinjector simulation embodiment and a removable injection simulation device apparatus embodiment having an agitator, associated therewith.

FIG. 8B is a perspective, partial view of an autoinjector simulation embodiment and a removable injection simulation device apparatus embodiment having an agitator, associated therewith.

FIG. 8C is a perspective, partial view of an autoinjector simulation embodiment and a removable injection simulation device apparatus embodiment having an agitator, removed therefrom.

FIG. 8D is a side view of an autoinjector simulation embodiment with a removable injection simulation device apparatus embodiment having an agitator, associated therewith.

FIG. 9A is a perspective view of an autoinjector simulation embodiment and a removable injection simulation device apparatus embodiment having multiple agitators associated therewith.

FIG. 9B is a perspective, partial view of an autoinjector simulation embodiment and a removable injection simulation device apparatus embodiment having multiple agitators associated therewith.

FIG. 9C is a perspective, partial view of an autoinjector simulation embodiment and a removable injection simulation device apparatus embodiment having multiple agitators removed therefrom.

FIG. 9D is a side view of an autoinjector simulation embodiment with a removable injection simulation device apparatus embodiment having multiple agitators associated therewith.

FIG. 10A is a perspective view of an autoinjector simulation embodiment and a removable injection simulation device apparatus embodiment having an agitator, associated therewith.

FIG. 10B is a perspective, partial view of an autoinjector simulation embodiment and a removable injection simulation device apparatus embodiment having an agitator, associated therewith.

FIG. 10C is a perspective, partial view of an autoinjector simulation embodiment and a removable injection simulation device apparatus embodiment having an agitator, removed therefrom.

FIG. 10D is a side view of an autoinjector simulation embodiment with a removable injection simulation device apparatus embodiment having an agitator, associated therewith.

FIG. 12A shows a perspective view of a distal end of an injection simulation device embodiment.

FIG. 12B shows a cross-section view of the distal end shown in FIG. 12.

FIG. 12C shows a bottom view of an alternative injection simulation device embodiment.

FIG. 12D shows a bottom view of an alternative injection simulation device embodiment.

FIG. 12E shows a bottom view of an alternative injection simulation device embodiment.

FIG. 12F shows a bottom view of an alternative injection simulation device embodiment.

FIG. 14A shows a partial cutaway view of a distal end of an injection simulation device embodiment.

FIG. 14B shows a cross-section view of the embodiment shown in FIG. 14A.

FIG. 15A shows a perspective, partial cutaway view of a distal end of an injection simulation device embodiment.

FIG. 15B shows a side, partial cutaway view of the embodiment shown in FIG. 15A.

DETAILED DESCRIPTION

Figure 1:
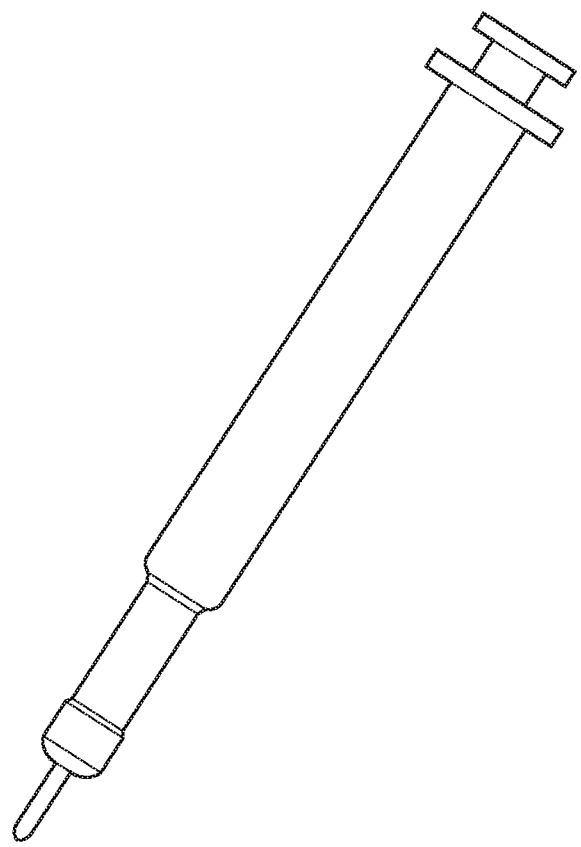
FIG. 1 includes a perspective view of an injection simulation device embodiment.

The inventors have found that a need exists for an injection training device which may be safely and efficiently used by patients and healthcare providers, both with and without medical experience alike, to use for practicing delivering an injection. Furthermore, the inventors have found that a device which closely resembles and simulates the look and feel of an injection device that can be used to simulate an injection for training purposes in order to increase injection compliance and decrease anxiety associated with delivering injections would be highly beneficial. The inventors have further identified the importance of the resettability of an injection training device, and furthermore, the critical requirement that the training device accurately simulate the needle-containing injection device. These goals, in addition to creating a safe training device which solves many of the issues found in the prior art are achieved by embodiments of the subject invention as provided herein.

Definitions

The term "injection device," as used herein, includes but is not limited to any device used to deliver medicament by way of parenteral administration. These injections include, but are not limited to intramuscular (IM), intravenous (IV), subcutaneous (SC), inravitreous, intraosseous infusion, intracerebral, intra-arterial, intracerebroventricular, intrathecal, among other injection types. The injection simulation device may include structural and/or functional features to simulate an auto injector in a non-limiting embodiment, or a prefilled syringe in another non-limiting embodiment, for example. Other injection devices may also be simulated by the injection simulation device embodiments described herein.

The term "injection simulation device" as used herein includes, but is not limited to, a device for simulating the use of an injection device.

The term "intervening component" as used herein includes, but is not limited to, a component for interfacing between two or more components. The intervening component may include, but is not limited to, a biasing member, a spacer, or a projection extending from a component of the device, in non-limiting embodiments.

The term "associated" or "association", as used herein, includes but is not limited to direct and indirect attachment, adjacent to, in contact with, partially or fully attached to, and/or in close proximity therewith. The term "substantially equal" as used herein, includes but is not limited to equal to or within a 0.1-10% variance.

Those skilled in the art will understand that the term gauge (G) refers to a gauge of a needle according to gauges known in the art. Typical gauge ranges used in the equation (s) provided herein will include gauges ranging between approximately 18-34.

During an injection, a user of an injection device having a needle encounters various forces. Oftentimes, the first force encountered is that which is required to traverse a first layer of tissue (oftentimes the skin) with the needle, the pressure required by the user on the needle until the needle traverses the user's first layer of tissue is called a deformation force, which is the force that deforms the skin until the needle punctures the skin. This force required increases as the skin becomes deformed. Following the deformation force, there is often a temporary and typically brief decrease in force on the needle during an injection, known as the puncture force, which is the force that occurs once the needle has traversed the skin, i.e., punctured the skin, and before the needle moves further into the tissue of the patient. A third force often encountered during an injection follows the puncture force, and is termed an insertion force. The insertion force is an increasing force on the needle as the needle traverses tissue of the patient to reach a target location in the patient required for the injection. The increase in force over time typical of the insertion force period occurs as the needle travels through the tissue and can be attributed to an increase in pressure on the needle as it passes through multiple layers of tissue on its trajectory to the target injection location in the patient. These forces are often surprising and unexpected to an inexperienced injection provider, whether it is a patient who is self-administering an injection or a medical personnel administering an injection to a patient, particularly when administering an injection for the first time. Therefore, it is beneficial to provide a simulation device to simulate forces a user would encounter when using the injection device, such that a seamless transition will occur between training with a simulation device, and using the injection device to deliver medicament. This seamless transition may decrease the occurrence of failed injections when using the medicament delivery device.

Embodiments of the invention as described herein are provided to accurately simulate these forces, among other features of an injection and an injection device to decrease anxiety associated with administering an injection.

In an embodiment, an injection simulation device is provided to allow for a simulated injection experience during use of the injection simulation device without puncturing the skin of a user. The injection simulation device may include an injection simulation member may include a blunt end probe, in one non-limiting embodiment. Other non-limiting embodiments of the injection simulation member are described in greater detail herein. The injection simulation member embodiments may be provided to simulate the look, feel, and/or sound of a needle during an injection, without puncturing the skin of the user. One skilled in the art would realize that the injection simulation member can be made of any materials known in the art to, in some embodiments, provide a flexibility, and tensile modulus to simulate a needle while maintaining the rigidity and stability to provide a simulated sensation of an injection without traversing the skin of the user. The injection simulation device provides a perception to a user of injection into the skin and mimics or simulates an actual injection during retraction of the injection simulation member from an extended position to a retracted position, in one embodiment, upon application of a force, to simulate an injection without traversing or puncturing the skin of the user.

In trying to simulate a medicament delivery or injection device, the device herein requires a force by the user for activation of the device (i.e., for initiating an injection). Multiple forces can be simulated by the device such as a force that is required (e g manual, spring loaded, electric motor, pneumatic cartridge, ultrasonic, or other type of force) to deliver a needle through tissue of a user using a prefilled syringe or other injection device, in non-limiting examples. In other examples, the forces similar to those encountered when using an auto injector or other injection device may be simulated with the injection simulation device embodiments described herein. The injection simulation device may simulate different forces in order to provide a simulated injection event by accurately simulating the forces encountered when using a medicament delivery device having a needle.

Embodiments of the injection simulation device may provide tactile, visual, and auditory stimuli to a user, wherein during use of the injection simulation device, the tactile, visual, gustatory, olfactory, or auditory feedback, or any combination thereof, are synchronized in a manner such that a needle-containing injection delivery device is accurately simulated. The synchronization of the stimuli is a significant factor in facilitating multisensory learning of the user.

Some of the injection simulation device embodiments described herein may include components which provide a tactile/force reflecting mechanism (i.e., resistance mechanism) to provide force feedback to simulate the feel of an injection device used during an injection, for example. Force feedback is typically accomplished by a tactile/force reflecting mechanism that imparts force to a user of the injection simulation device in response to manipulation of the injection simulation device. The force(s)/resistances that may be generated as a user manipulates the injection simulation device against a surface simulate the forces/resistances encountered during an injection at a target location of a user.

Multiple forces are encountered during an injection, and these forces are often influenced by one or more variables including needle gauge, needle length, injection angle needle point, needle coating or other surface characteristics, lubrication of needle or injection site, needle depth in patient tissue, type of patient tissue (i.e., skin, muscle), characteristics of patient tissue which may be influenced by age, health, weight, and/or genetically determined variables, among other potential force-influencing variables.

Forces that may be encountered during an injection are simulated in embodiments of the injection simulation device provided herein. Forces that may be encountered during an injection include a deformation force, a puncture rebound force, an insertion force, a relaxation force, and an extraction force or any combination thereof. A deformation force may occur when a needle is pressed onto a surface of a tissue, for example, an outer surface of the epidermal layer of a patient, causing the epidermis to deform under the pressure of the needle prior to puncture of the epidermis by the needle. A puncture rebound force refers to the force that is sensed once the needle traverses the tissue of the subject. It has been discovered that this causes a temporary decrease in force during an injection. An insertion force can be described as the force of the injection after the needle traverses the tissue, and until the needle reaches its target depth in the patient tissue. In some instances, the insertion force is the greatest increase in force over time during the course of an injection. A relaxation force typically follows the insertion force. The relaxation force occurs once the needle has reached its target depth in the patient tissue and the medicament is injected into the target tissue. The relaxation force is marked by a decrease in force that occurs as the medicament is expelled through the needle. An extraction force is one which is felt during removal or retraction of the needle from the tissue, and is marked by a greater decrease in force over time than the relaxation force, in some non-limiting instances.

Embodiments of the resistance mechanism described herein may include different components in different embodiments. In non-limiting embodiments, the resistance mechanism may include multiple components, such as, a combination of structural features of the injection simulation device which move relative to one another to produce a resistance during a simulated injection which mimics the forces encountered by a user during an injection with an injection device, for example. The resistance produced may be controlled by manipulating the shape(s) of one or more of the structural features, or the surface(s) characteristics of the one or more structural features, or the material(s) of the one or more structural features, in non-limiting embodiments.

The resistance mechanism may, in an embodiment, include a material traversable by a needle, for example, to produce a varying resistance to mimic the forces and the tactile feel of an injection. This traversable material may be disposed within the housing of the injection simulation device or on an outer portion thereof. Traversal of the needle through the traversable material may provide a tactile feel of a needle traversing a tissue of a subject during an injection. Furthermore, the traversal may be viewable by the user of the device, providing a visual and tactile representation to simulate an injection event. The material may include a rubber or septum material, or a pseudo-skin material, in non-limiting embodiments, to further enhance the simulation of penetrating tissue.

In another embodiment, a resistance mechanism may include a pneumatic system, wherein a build-up of air in the injection simulation device housing occurs as the injection simulation member is retracted, so as to cause a pneumatic resistance to the retraction of the injection simulation member to simulate an injection.

In one embodiment, an injection simulation device having a housing comprising a proximal end and a distal end, a plunger comprising a proximal end and a distal end and being slidable relative to the housing, a retractable injection simulation member at the distal end of the housing, the retractable injection simulation member being movable between an extended position and a retracted position, at least one biasing member, wherein the biasing member is associated with the retractable injection simulation member, and directly or indirectly associated with the plunger; wherein a force on a distal end of the injection simulation member causes movement of the injection simulation member from an extended position to a retracted position, to compress the first biasing member, and simulate the tactility of an injection to a user; and wherein a force on the proximal end of the plunger asserts a force on the first biasing member to reset the injection simulation member to the extended position is provided. The retractable injection simulation member configured to simulate a needle of an injection device with a determined gauge (G) and which device is configured such that the injection simulation member retracts from an extended position to a first retracted position under application of a $force_1$ (N), to simulate a deformation force ($Force_d$) according to the formula $Force_d = C(-0.046(G)+1.83)$, wherein the force value ranges between +/−1%-30% and every integer in between, and wherein C comprises a coefficient, said coefficient being a factor of the deformation force of the injection simulation device. In another embodiment, the force value ranges +/−1%-20% and every integer in between. In yet another embodiment, the force values ranges +/−1%-10% and every integer in between. The value of C is further defined below. In one non-limiting embodiment, the value of C may include a value between 0.2-3.6.

In a further embodiment, the retraction of the injection simulation member from the extended position to the first retracted position comprises a force determined by the formula $F(x)=K*X^P$ wherein $F(x)$ is a force value at a point between the extended position and the first retracted position, K is a resistance value including a resistance of the injection simulation device, X is a displacement value, and P is an exponential power value greater than zero. $F(x)$ may be a force value simulating a deformation force in one embodiment. In another embodiment, $F(x)$ may be a force value simulating an insertion force.

In an alternative non-limiting embodiment, $F(x)$ is a force value at a point between the extended position and at least a second retracted position. $F(x)$ denotes F as a function of (x). In non-limiting embodiments described herein, $F(x)$ denotes a Force at point x.

In another embodiment, the injection simulation device is provided wherein the deformation force $F_d$ depends on one or more factors including: a composite area of injection value (C1), a bevel of the needle value (C2), lubrication of the needle or an injection site value (C3), and/or injection angle (C4) wherein a force of the device is determined by the formula $C=C1*C2*C3*C4$.

In one embodiment, the C1 value includes a higher value when the composite area of injection includes a more dense tissue area and a lower value when the composite area of injection includes a less dense tissue area. For example, muscle tissue includes a more dense tissue than in adipose tissue; consequently, the C1 value would be higher for muscle tissue than it would be for adipose tissue. In one non-limiting example, when the composite area of injection includes a subcutaneous tissue, the C1 value ranges from 0.5-2.0.

In a further embodiment, the injection simulation device may be configured to simulate a force based on a needle bevel, wherein the C2 value is higher when a needle with a bevel that creates a larger angle at a distal end of the needle is simulated, and lower when a needle with a bevel that creates a smaller angle at the distal end of the needle is simulated. In a non-limiting example, the C2 value ranges from between 0.5-1.5.

In still a further embodiment, the injection simulation device may be configured to simulate a force based on lubrication or non-lubrication of a needle or an injection site, and wherein the C3 value is higher when an un-lubricated needle and/or injection site is simulated and lower when a lubricated needle and/or injection site is simulated. In one non-limiting example, the C3 value ranges from between 0.5-1.0.

In yet a further embodiment, the C4 value decreases when a longitudinal axis of the injection simulation member is generally perpendicular to a plane in which a surface including the injection site is disposed, and increases when an angle between the longitudinal axis of the injection simulation member and the plane in which the surface including the injection site decreases. In a non-limiting example, the C4 value includes 1.0 when the angle between the longitudinal axis of the injection simulation member and the plane of the surface including the injection site comprises 90 degrees. In another non-limiting example, the C4 value includes 1.4 when the angle between the longitudinal axis of the injection simulation member and the plane of the surface including the injection site comprises 45 degrees.

The exponential value, P, is a value that may affect the change in force exponentially, where as the P value increases, the force value may increases exponentially. In a non-limiting embodiment, the P value may range between 0.5 and 4.

The displacement value, X, is a position of the injection simulation member as it moves between extended and retracted positions. In one non-limiting embodiment, the X value ranges between 0.000001 mm and 250 mm.

In an embodiment, an injection simulation device for simulating one or more forces of an injection, the device including a housing; and a retractable injection simulation member associated with the housing, configured to simulate a needle of an injection device with a determined gauge. The device is configured such that the injection simulation member retracts from an extended position to a retracted position upon application of a force according to a multi-phase force profile. The multi-phase force profile may include at least a first phase configured to simulate a deformation force, the deformation force simulating the force of pressing a needle against a subject so as to deform at least a first layer of tissue prior to puncturing at least the first layer of tissue of the subject; and at least a second phase configured to simulate a puncture rebound force, in a non-limiting embodiment. In one embodiment, the second phase includes a force that is less than the deformation force.

The device may further include at least a third phase configured to simulate an insertion force, wherein the insertion force includes the force required for a needle to traverse the tissue to a target injection location of the subject. The target injection location includes a location wherein the injection is to occur, such as, muscular tissue, intra-ocular tissue, subcutaneous tissue, adipose tissue, intra or inter peritoneal tissue, inter or intra venous or arterial tissue, among other target locations for injections known to those skilled in the art.

In a further embodiment, the injection simulation device includes one or more additional phases configured to simulate puncturing of composite tissue areas. Composite tissue areas may include multiple layers of tissue that may be traversable, wherein multiple deformation, puncture, and insertion forces are required to reach the target location for the injection. Certain procedures such as an amniocentesis, for example, used in prenatal diagnosis of chromosomal abnormalities, fetal infections, or sex determination from a sample of amniotic fluid containing fetal tissues retrieved from the amniotic sac using a needle in the procedure, require passage through multiple layers of tissue to reach the target location. These procedures may include multiple phases and multiple forces which are experienced and which may be simulated in embodiments of the injection simulation device provided herein.

In a further embodiment, an injection simulation device configured to simulate forces applied to an injection device during an injection event includes a housing, an injection simulation member, the injection simulation member is configured to be retracted from an extended position to a first and/or second retracted position in response to a force on said injection simulation member. The injection simulation device further includes a resistance mechanism, wherein the resistance mechanism may provides one or more resistance values (one or more forces) as the injection simulation member is retracted, to simulate one or more forces applied during an injection event. The resistance may increase as the injection simulation member is retracted to simulate a deformation force until at least a first retracted position is reached, wherein upon reaching the first retracted position, the resistance decreases to simulate a puncture rebound force, following the decrease in resistance, the resistance increases as the injection simulation member is retracted to simulate an insertion force until at least a second retracted position is reached, wherein said one or more forces are configured to simulate one or more variables affecting one or more forces during an injection, including needle gauge, needle length, needle bevel, needle coating, needle sharpness, lubrication of the needle, angle of the needle relative to a target site, or one or more characteristics of a tissue traversed by a needle, or a combination thereof.

In a further embodiment, the resistance mechanism may include a first engaging component having a first interfacing surface and a second engaging component having a second interfacing surface, the first and second interfacing surfaces being configured to interface with one another, wherein an interface between the first and second engaging components is configured to provide a resistance on a movement of the first engaging component and the second engaging component relative to one another. The first engaging component may be associated with a portion of the injection simulation member and the second engaging component may be associated with a portion of the housing, wherein a force is required to move one of the first engaging component or the second engaging component relative to the other of the first engaging component or the second engaging component when contact is made between the first interfacing surface and second interfacing surface, said force simulating a deformation force and/or an insertion force of an injection.

The device may further include a biasing member for providing a resistance on the retraction of the injection simulation member. In a further embodiment, the resistance provided by the biasing member during retraction of the injection simulation member to at least the first retracted position simulates the deformation force of an injection, and wherein the first and second engaging components move relative to one another as the injection simulation member is retracted to at least the second retracted position to provide a resistance to simulate an insertion force.

In another embodiment, the resistance mechanism includes a digressive spring. In a further embodiment, the digressive spring comprises a Belleville spring, wherein the Belleville spring is compressed as the injection simulation member is retracted and a resistance on the retraction of the injection simulation member increases until the Belleville spring reaches a threshold compression level, wherein upon reaching the threshold compression level, the resistance on the injection simulation device decreases.

In still another embodiment, the resistance mechanism may include a needle component and a needle-traversable material, wherein upon exerting a force on the injection simulation member to retract the injection simulation member from an extended position to a retracted position, the needle component traverses the needle-traversable material to provide a tactile feedback and/or a resistance to simulate the feel of a needle traversing a tissue of a patient. In one particular embodiment, the needle-traversable material may include a pseudo skin material.

In a further embodiment, the resistance mechanism may include a resistance membrane disposed within the housing such that the injection simulation member contacts the resistance membrane as the injection simulation member is retracted from an extended position to a retracted position in response to a force on the injection simulation member. During retraction of the injection simulation member, the movement of the injection simulation member relative to the resistance membrane provides a resistance on the injection simulation member to simulate a deformation force and/or an insertion force of an injection. Upon releasing the force on the injection simulation member, the biasing member may cause the injection simulation member to be extended from a retracted position to an extended position to reset the injection simulation device.

In another embodiment herein, a method for simulating an injection on a user with an embodiment of the injection device is provided herein. In a further non-limiting embodiment, a method for simulating an injection comprising applying an injection simulation device to a location on a subject, wherein the device comprises a retractable injection simulation member and is configured such that a force applied to retract the injection simulation member is representative of an actual injection device. In an alternative embodiment, non-linear forces are required to retract the needle thereby simulating insertion in one or more layers of tissue. In still a further non-limiting embodiment, a method for simulating an injection comprising providing differential resistances based on, injection angle, needle length, needle point, needle coating, lubrication of needle or injection site, needle depth into composite tissue, or a combination thereof is provided herein.

The inventors have determined herein that resetting an injection simulation device that accurately simulates the tactility of an injection device is complicated. In order to mimic the tactility of the injection device in the injection simulation device, while providing a resettable training device, several mechanical and logistical considerations are required. Other benefits for an injection training device may include simulating the speed at which the medicament is delivered to the user through a needle, in one non-limiting embodiment. The inventors have herein discovered an injection simulation training device, which accurately simulates the speed at which medicament is delivered through a needle to a user, such that by training with the injection simulation training device, the user is primed to use the drug delivery device. The injection simulation training device functions to minimize or eliminate any differences between a training device and a drug delivery device, such that training with the injection simulation training device, a user can anticipate what will occur when the drug delivery device is used.

Figure 2A:
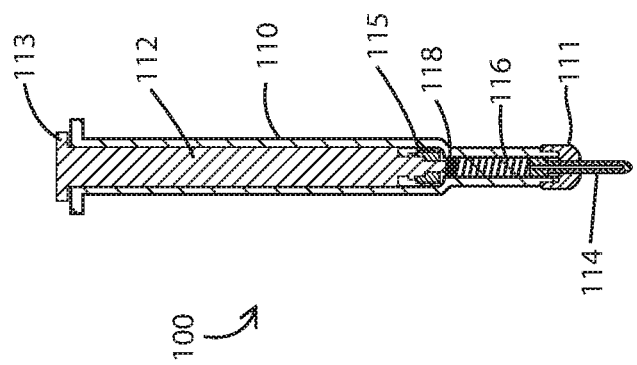
FIG. 2A-C include cross sectional views of the injection simulation device embodiment of FIG. 1.
Figure 2B:
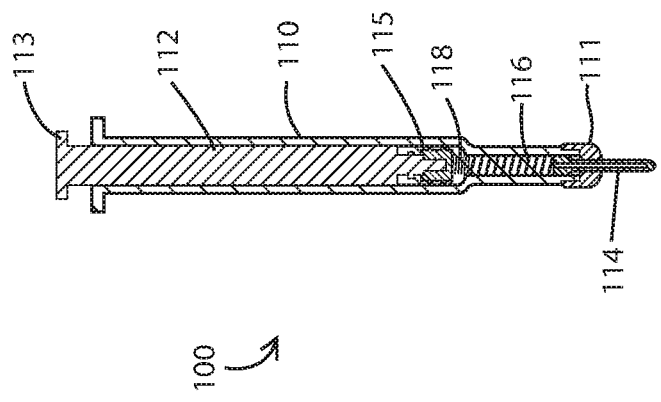
Figure 2C:
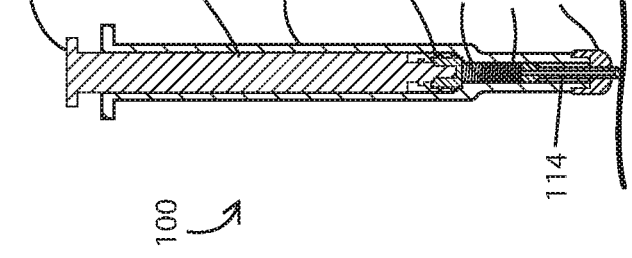

Turning to the Figures, FIG. 1 is a perspective view of an injection simulation device embodiment 100, and FIGS. 2A-C are cross sectional views of the injection simulation device embodiment 100 shown in FIG. 1. The injection simulation device embodiment 100 includes a housing 110 having a proximal end 109 and a distal end 111. The injection simulation device embodiment 100 further includes a plunger 112 having a proximal end 113 and a distal end 115 and being slidable relative to the housing 110, in a non-limiting embodiment. The injection simulation device embodiment 100 further includes an injection simulation member 114 configured to simulate a needle of an injection device, and at least one biasing member 116. At least one biasing member 116 may be associated with the injection simulation member 114. The injection simulation member 114 is retractable, and is associated with the housing distal end 111. The at least one biasing member 116 may be directly or indirectly associated with the plunger 112. In the injection simulation device embodiment shown in FIGS. 2A-C, the at least one biasing member 116 is indirectly associated with the plunger 112 via a second biasing member 118. In an alternative embodiment, the injection simulation member 114 may be associated, either directly or indirectly with the plunger 112. The injection simulation member 114 may be movable between an extended position and a retracted position upon an application of a force on its distal end, to simulate the use of an injection device. One or more forces or resistances sensed by a user during the use of an injection device may be simulated with the injection simulation device 100 with the use of a biasing member 116 and a retractable injection simulation member 114, for example, insertion force, puncture force, puncture rebound force, deformation force, and/or a combination of these forces. Therefore, the tactility of an injection is simulated to the user by use of the injection simulation device 100. Other features and functions as described in further detail herein provide additional simulation properties, such that when using the injection simulation device 100, a user experiences an emotional and psychological experience that is similar to the experience that is had when using the injection device.

In instances when the first biasing member 116 is indirectly associated with the plunger 112, one or more intervening components may be provided to interface between the plunger 112 and the first biasing member 116. The intervening component may be associated with either the plunger 112 or the first biasing member 116, or may be disposed there between. In the embodiment shown in FIG. 2A-C, the intervening component includes a second biasing member 118.

The injection simulation device 100 is resettable. To simulate an injection with the injection simulation device, a user presses the distal end of the injection simulation member 114 against a target surface of the user, such that the injection simulation member 114 retracts into the distal end of the housing 111. By doing so, the first biasing member 116 is activated, and an injection simulation event occurs. The user senses the one or more forces/resistances felt during an injection with an injection device during this process. Following retraction of the injection simulation member 114, the plunger 112 may be slid relative to the housing 110 to simulate the movement of the plunger in an injection device, used to deliver medicament through a needle. Once the injection simulation member 114 is released from the target area of the user, the first biasing member 116 causes the injection simulation member 114 to extend. In some instances, however, a resetting mechanism is required to fully reset the injection simulation member 114 to a pre-use position. By moving the plunger 112 further toward the distal end of the housing 111, an interaction between the plunger 112 and the first biasing member 116, directly or indirectly via an intervening component (i.e., second biasing member 118, in a non-limiting example), or an interaction between the plunger 112 and the injection simulation member 114 (not shown in FIG. 2) causes the injection simulation member 114 to be fully reset to its pre-use position.

In one embodiment, an injection simulation device 100 includes a housing 110 having a proximal end 109 and a distal end 111. A plunger 112 may be slidable relative to the housing, and within the housing 110 as shown in FIGS. 2A-C. A retractable injection simulation member 114 may be associated with the distal end of the housing 111, wherein the member is movable between an extended position and a retracted position. A retracted position is shown in FIG. 2A, in a non-limiting example, and an extended position is shown in FIG. 2B. FIG. 2C provides a view of the member in a fully reset, extended position. The device 100 includes at least one first biasing member 116, wherein the member 116 is associated with the retractable injection simulation member 114, and directly or indirectly associated with the plunger 112. In FIG. 2A, the plunger 112 is shown as indirectly associated with the first biasing member 116 via an intervening component, a second biasing member 118, in the non-limiting embodiment shown. A first force on a distal end of the injection simulation member 114 causes movement of the injection simulation member 114 from an extended position to a retracted position, to compress the first biasing member and simulate the tactility of an injection to a user, as shown in FIG. 2A, wherein a second force on the proximal end of the plunger 112 asserts a third force directly or indirectly on the first biasing member 116 to facilitate resetting the injection simulation member 114 to the extended position, (FIG. 2C), in one embodiment.

In some embodiments, the plunger may interface directly with the first biasing member 116 to reset the injection simulation member 114. Various types of intervening components may be used to effect reset of the injection simulation member, in some embodiments. In still other embodiments, the plunger may interface directly with the injection simulation member 114 to reset the member 114.

In one non-limiting embodiment, a release of the first force on the distal end of the injection simulation member 114, optionally in combination with the second force on the proximal end of the plunger, allows the first biasing member to expand, causing the injection simulation member to extend.

In one non-limiting embodiment, the at least one first biasing member 116 may be configured to provide a resistance simulating a deformation force and/or an insertion force of a needle during an injection event upon applying the first force. In one non-limiting embodiment, the first biasing member 116 may comprise a digressive spring, for example. In a further embodiment, the retractable injection simulation member comprises a proximal end associated with the device, and a distal end, wherein the distal end comprises an agitator having an agitator base portion associated with the distal end, an agitator tip, and an agitator body between the base portion and the agitator tip. In still a further non-limiting embodiment, the agitator body is between 1.0-3.0 mm in length. In another non-limiting embodiment, the agitator body comprises a tip portion located 0.2-0.5 mm proximally from the agitator tip. In another non-limiting embodiment, the surface area of a transverse plane along the body ranges from [0.03-10 mm$^2$]. In still a further non-limiting embodiment, a surface area of a transverse plane of the base portion is greater than a surface area of a subjacent transverse plane of the body or a transverse plane of the tip portion. In yet a further non-limiting embodiment, a surface area of a transverse plane of the base portion is substantially equal to a surface area of a subjacent transverse plane of the body or a transverse plane of the tip portion. In another non-limiting embodiment, the surface area of a transverse plane of the tip portion ranges between 0.03-3.5 mm$^2$.

In another embodiment, as shown in FIGS. 3A-3B, an autoinjector simulation device embodiment 200 is shown. FIG. 3A provides a side view of an autoinjection simulation device embodiment 200 including a housing 210 with a proximal end 209 and a distal end 211. At least one agitator 214 is provided at the distal end 211 of the device. The agitator 214 comprises an agitator base portion 220 associated with the distal end of the device 200, an agitator tip 216, and an agitator body 223 between the base portion 220 and the agitator tip 216. The agitator is configured to associate with the distal end of the device 200, such that the agitator 214 contacts a surface of a user to simulate the tactile feel of a needle during an injection without puncturing the surface. In an embodiment, the agitator body 223 may include a length of between 1.00 mm-3.0 mm. In another embodiment, the agitator body 223 may include a tip portion 222 located 0.2-0.5 mm proximally from the agitator tip 216. The agitator may include properties configured to cause discomfort and/or pain to a user during use, without puncturing the skin of the user. In addition to the dimensions provided herein, these properties may include varying surface textures or shapes of the agitator, or, more specifically, of the agitator tip portion, in non-limiting embodiments. In some non-limiting embodiments, the surface area of a transverse plane along the body 223 ranges from [0.03-10 mm$^2$]. In other non-limiting embodiments, a surface area of a transverse plane of the base portion 220 is greater than a surface area of a subjacent transverse plane of the body 223 or a transverse plane of the tip portion 222.

In still a further non-limiting embodiment, a surface area of a transverse plane of the base portion 220 is substantially equal to a surface area of a subjacent transverse plane of the body 223 or a transverse plane of the tip portion 222.

In some non-limiting embodiments, the at least one agitator 214 is removably associated with the injection simulation device 200, 100.

In various other embodiments shown in the Figures, placement of agitators are shown in varying locations on the device. As aforementioned, the agitator may be used to simulate the sensation felt by a user during an injection without puncturing the skin of the user. Consequently, the agitator may be formed so as to create a sense of pain or discomfort in a user, without damaging the target surface of the user, in one embodiment. In order to accurately simulate the injection experience, embodiments the injection simulation device are configured herein to simulate various types of injection devices.

Injection devices, particularly auto injector devices, include various configurations and differing means of actuation to effect injection. For example, in some embodiments, autoinjector devices are actuated by activation of a button, meaning that the injection process occurs by activation of the button. These devices can be broken down into two general categories. The first category includes devices which are button actuated, but the needle insertion component of the injection is manual. In this type of auto injector device, the button causes the medicament to be delivered to the user, but insertion of the needle is manually accomplished by the user by placing the injection device against the target area of the user. The second category includes button actuated devices, wherein the needle is inserted automatically. Upon activating the actuation member (i.e., button) the needle is inserted into the skin of the user, and medicament is delivered through the needle. Other types of auto injector devices include actuation with the use of a safety shield. These devices can also be broken down into two categories. The first category of shield-actuated devices includes those where the needle is inserted into the skin of the user manually. In this type of device, as the user presses the device against the target area, the needle shield is retracted, and the needle beneath the shield is inserted into the user. The second category of shield-actuated devices includes the automatic needle insertion device. In this type of device, the shield is pressed against a target surface of a user, and upon retraction of the shield, the needle is ejected into the user's skin and medicament is delivered through the needle.

The inventors have discovered an ability to simulate the tactile feel of an injection sensed when using the aforementioned devices. The particular arrangements of the injection simulation devices are shown in the Figures below. Exemplary embodiments of the injection simulation device described herein include a proximal and a distal end, and at least one agitator for associating with the distal end of the device, such that the agitator contacts a surface of a user to simulate the tactile feel of a needle during an injection without puncturing the surface of the user.

In some embodiments provided herein, injection simulation devices are provided to simulate manual needle insertion devices. For example, in FIGS. 4A-C and 5A-C, one or more agitators are provided on a safety shield as shown in embodiments 300 and 300'. In the embodiments shown in FIGS. 4A-C, an agitator 314 (plurality of agitators 314 shown in FIG. 4A and the alternative of just one agitator shown in FIG. 4B) is provided on the safety shield 312 to simulate the tactility of an injection during use of the device. In the perspective views of FIGS. 4A-B and the side view of FIG. 4C, an injection simulation device embodiment 300 is provided having a housing 310, wherein a proximal end of the housing 309 and distal end of the housing 311 is shown. A safety shield 312 is associated with a distal end of the housing 311, and an actuation member 316 is associated with the proximal end of the housing 309. The device embodiment 300 shown in FIGS. 4A-C demonstrate a device 300 in which a manual needle insertion drug delivery device is simulated. FIGS. 5A-C show another embodiment 300 of the device shown in FIGS. 4A-C, wherein multiple agitators 314 are disposed on the safety shield 312'. The device embodiment 300' of FIGS. 5A-B also includes a housing 310 having a proximal end 309 and a distal end 311, wherein an actuation member is associated at the proximal end 316. In addition to the agitators 314 shown on the safety end shield 312 in FIGS. 4A-4C, or as an alternative thereto, one or more agitators may be provided on an injection simulation member 313 as shown in FIGS. 4A-4B. The injection simulation member 313 may be activated upon actuation of the device, following activation of the actuation member at the proximal end 316, for example, causing the injection simulation member 313 to be delivered toward the distal end 311 of the device.

The injection simulation device embodiments 400 and 400' shown in the perspective views of FIGS. 6A-B and the side view of FIG. 6C, and in the perspective views of FIGS. 7A-B and the side view of FIG. 7C, respectively, simulates an automatic needle insertion device. The injection simulation device embodiment 400 of FIGS. 6A-C includes an outer housing 410 having a proximal end 409 and a distal end 411, and an actuation member 407 associated with the proximal end 409. The injection simulation device embodiment 400 also includes an inner housing 412 having a proximal end 415 and a distal end 414. A safety shield 418 having a notch 420 is associated with the housing distal end 411. The shield 418 (shown in a retracted position) is retractable and extendable relative to the housing 410. The inner housing distal end 414 comprises an agitator 416 thereon. The notch 420 of the shield 418 is configured to interface with the agitator 416 during the use of the device 400. During use, the distal end 411 of the device 400 is pressed against a target surface of a user, such that the shield 418 is retracted, into the outer housing 410. Upon either: 1) retraction of the shield 418 or 2) actuation of the actuation member 407 (optional), the agitator 416 contacts the target surface of the user to simulate the tactility of a needle puncturing the skin of the user.

FIGS. 7A-B provide a perspective view, and FIG. 7C provides a side view of an embodiment 400', having an outer housing 410, with a proximal; end 409 and a distal end 411, and an option actuation member 407. The device embodiment 400' includes an inner housing 412' having a proximal end 415 and a distal end 414'. The distal end 414' of the inner housing has multiple agitators 416 associated therewith. The device embodiment 400' may further include a safety shield 418' comprising multiple notches 420 at its distal end. The safety shield 418' is associated with the outer housing distal end 411, and is retractable and extendable relative thereto. Each notch 420 is configured to interface with a respective agitator 416 during use of the device. As with the embodiment shown in FIG. 6, during use, the device 400' is placed against a user target surface, such that the safety shield 418' is retracted into the device 400', and upon either: 1) retraction of the shield 418' or 2) actuation of the actuation member 407 (optional), the agitators 416 contact the target surface of the user to simulate a needle puncturing the skin of the user and simulate the tactility observed by a user during use of an automatic needle insertion auto injector device.

FIGS. 8A-C include perspective views, and FIG. 8D includes a side view of a further embodiment of an injection simulation device 500. The device 500 includes an outer housing 510 having a proximal end 509 and a distal end 511, and an inner housing 512 having a proximal end 515 and a distal end 513. The inner housing distal end 513 may be configured to receive a removable apparatus 514 that associates with the injection simulation device 500. The apparatus 514 includes a device interfacing portion 519 that secures the apparatus 514 to the injection simulation device 500. The apparatus also includes at least one agitator 516, wherein operation of the injection simulation device exposes the at least one agitator so as to interact with a surface of a user, the agitator configured to simulate the tactility of a needle without puncturing the surface. The device 500 may include a safety shield 518 with a notch 520 for interfacing with the agitator 516 during operation of the injection simulation device, in one non-limiting embodiment. The apparatus 514 may include a ring-like shaped interfacing portion 519 for interfacing with a portion of the injection simulation device 500. In one non-limiting embodiment, the ring-like portion may interface with the inner housing distal end 513 as shown in FIG. 8B. One or multiple agitators 516 (as shown in FIGS. 9A-D) may be spaced around the circumference of the ring like body 514, projecting away from the device interfacing portion 519.

FIGS. 9A-D provide another embodiment 500' similar to the embodiment of the device 500 in FIG. 8, however, the safety shield 518' is provided with multiple notches 520, and the removable apparatus 514' and a device interfacing portion 519, comprises multiple agitators 516, each of which may interface with a respective notch 520 when the injection simulation device is in use.

In another non-limiting embodiment, shown in FIGS. 10A-D, an injection simulation device 600 is provided. The device 600 comprises an outer housing 610 with a proximal end 609 and a distal end 611, and an inner housing 612 with a proximal end 615 and a distal end 613. An optional safety shield 619 may be provided, and may include a notch 614 to interface with an agitator 618, in one non-limiting embodiment. The inner housing distal end 613 may interface with a removable injection simulation device apparatus 617 having an agitator 618. The inner housing distal end may include a notch 614 for interfacing with the agitator 618 of the apparatus 617. The apparatus 617 may include a body 616 having a device interfacing portion 621 for interfacing with the inner housing distal end 613 when the apparatus is attached thereto.

Figure 11:
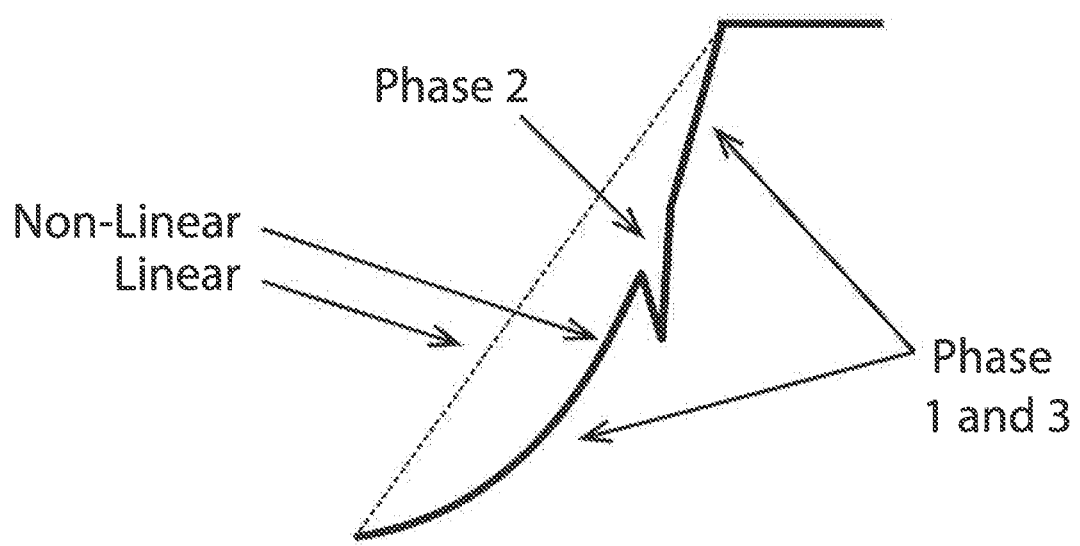
FIG. 11 is a graph illustrating an example of a multi-phase force profile of an injection.

FIG. 11 provides a graph illustrating an example of a multi-phase force profile of an injection, including a first phase, a second phase and a third phase, in a non-limiting embodiment. The multi-phase force profile may be simulated by embodiments of the injection simulation device as described herein. The first phase may simulate a deformation force, the second phase may simulate a puncture force, or a puncture force and puncture rebound force, and the third phase may simulate an insertion force of an injection, in non-limiting embodiments.

FIGS. 12A-12B show a perspective view of a distal end of an injection simulation device embodiment 700 and a cross-section view of the distal end of embodiment 700, respectively. As shown in FIG. 12A, the embodiment 700 includes an agitator on the distal end of a safety shield 714. The safety shield 714 is retractable relative to outer housing 710. The embodiment 700 also includes an inner housing 712 with a plunger 709 disposed therein. The plunger 709 is slidable relative to the inner housing 712. Disposed on the bottom of the safety shield is an agitator 716 comprising a round nub. FIG. 12C shows an alternative embodiment 700' having an alternative agitator 716' representing a projection having a discontinuous perimeter (e.g. star shape). The discontinuous perimeter may external or internal. When internal, there is a channel into which the discontinuous pattern projects. When external, the discontinuous pattern projects outwardly. The discontinuous pattern provides a heightened tactility to simulate a needle puncture. FIG. 12D shows a bottom view where the agitator is fixed to a plunger portion such as that described in FIGS. 13A-B. FIG. 12E shows a bottom view of a pointed agitator 716'''. FIG. 12F shows an agitator 716'''' that is a rounded nub.

Figure 13A:
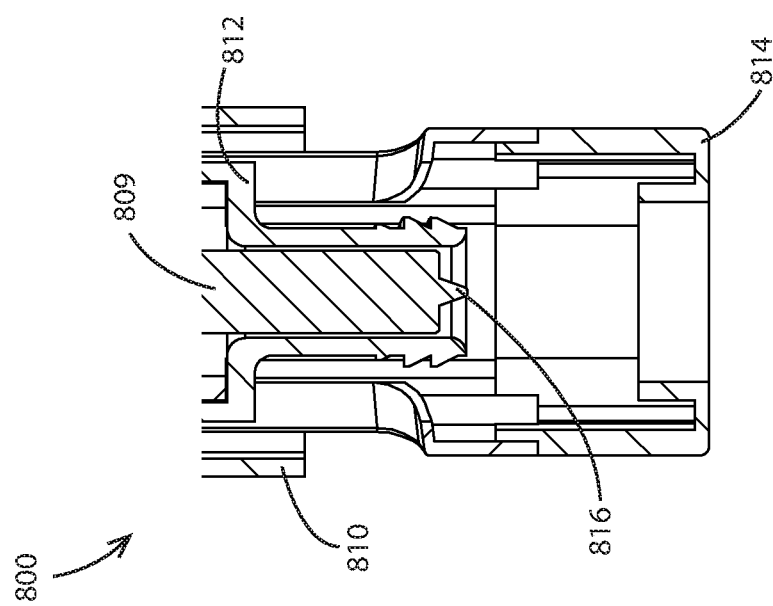
FIG. 13A shows a cross-section view of distal end of an injection simulation device embodiment.
Figure 13B:
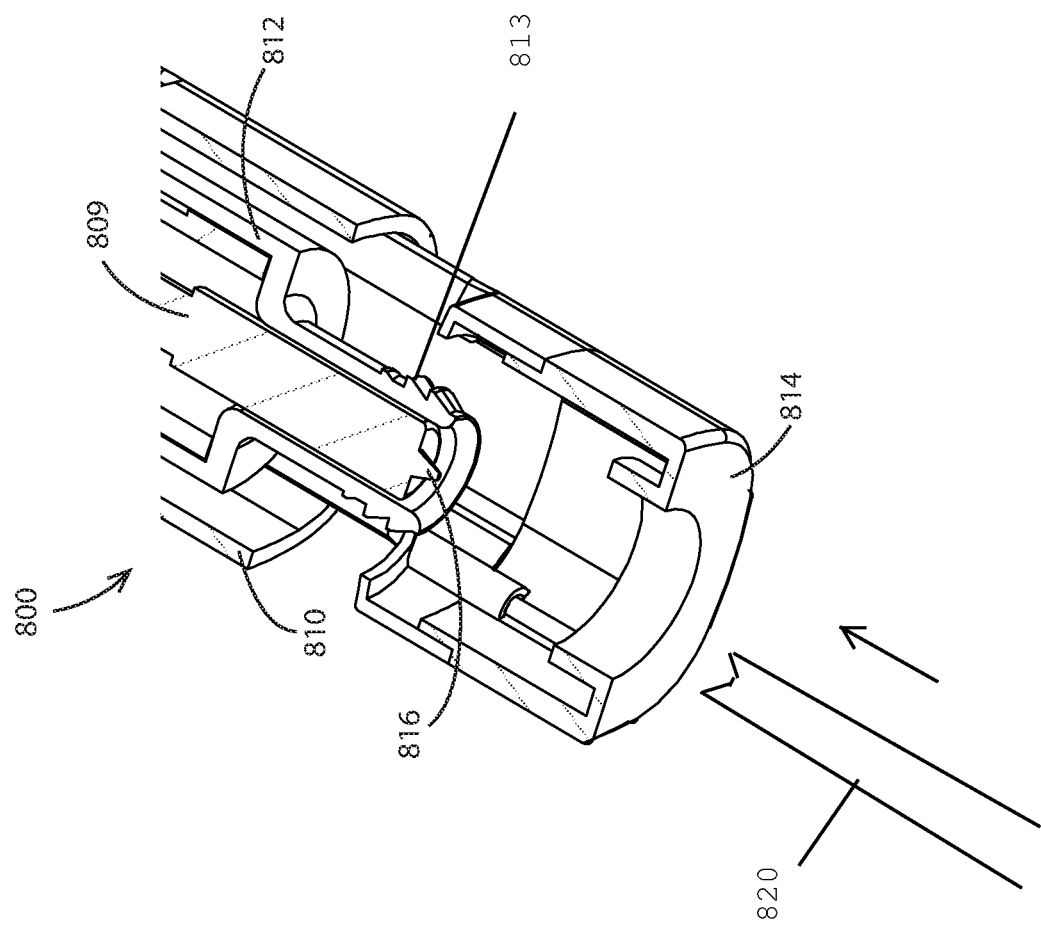
FIG. 13B shows a cross-section view of the embodiment of FIG. 13A with a reset member.

FIGS. 13A-B, show a cross-section view of distal end of an injection simulation device embodiment 800. Embodiment 800 includes an outer housing 810, and a safety shield 814 that is slidable relative to the outer housing 810. The embodiment 800 also includes an inner housing 812 and a plunger 809 that is slidable relative to the inner housing. The inner housing 810 also includes a threaded portion 813 on an outer surface of the distal end of the inner housing 810. On a distal end of the plunger 809 is a fixed agitator 816. Upon actuation of the embodiment 800, the plunger extends out the distal end of the safety shield 814 whereby the agitator 816 contacts the skin of a user to simulate the tactility of a needle. As shown in FIG. 13B, the embodiment 800 may further comprise a reset member 820 that interfaces with the distal end of the plunger 809. Upon application of force onto the plunger 809 by the reset member 820, the device is reset to allow for subsequent actuation of the embodiment 800. On the proximal end of the reset member 820, is a notch that interfaces with the agitator 816.

FIG. 14A-B shows a partial cutaway view and a cross-section view, respectively, of a distal end of an injection simulation device embodiment 800'. The embodiment 800' includes a slidable safety shield 814, an inner housing 812, a slidable plunger 809 and outer housing 810 similar to embodiment 800. On the distal end of the plunger 809 is a retractable agitator 816' that interacts with a retractable agitator biasing member 817 (e.g. spring). Furthermore, the inner housing 812 includes a threaded portion 813 disposed on an outer surface of its distal end. Optionally, a reset member similar to that shown in FIG. 13B can be implemented to execute a reset of the device embodiment 800'.

Figure 16:
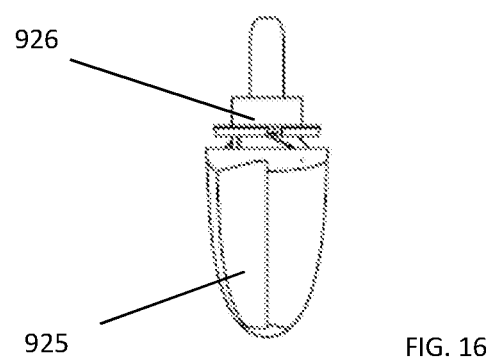
FIG. 16 shows a side view of a cap embodiment that is interactive with the embodiments shown in FIGS. 12-15.

FIGS. 15A-B show a partial cutaway view of a distal end of an injection simulation device embodiment 900. The embodiment 900 includes an outer housing 910, an inner housing 912 and a safety shield 914. The inner housing 912 includes a threaded portion 913 on an outer surface thereof. It is noted that the threaded portions 913, and 813 shown in FIGS. 13 and 14 are interactable with an optional cap 925 (shown in FIG. 16) that contains a threaded portion (not shown) on an inner surface of collar portion 926. The distal end of the inner housing 912 has an angled surface 916 that serves as an agitator. The agitator 916 interacts with a user's skin upon actuation of the device embodiment 900 to give tactility of a needle.

In another non-limiting embodiment, a method for simulating an injection is provided including providing an injection device having a housing and an injection simulation member slidably engaged with the housing, applying a force to a distal end of the injection simulation member to retract the injection simulation member from an extended position, wherein the force applied to the distal end of the injection simulation member is sufficient to overcome differential resistances of the injection device, and said force is representative of a force required for application on an injection medicament delivery device, and wherein the differential resistances are provided based on a multi-phase profile configured to simulate a first phase configured to simulate a deformation force of pressing a needle against a subject so as to deform at least a first layer of tissue prior to traversing at least the first layer of tissue of the subject, a second phase configured to simulate a puncture rebound force, and a third phase configured to simulate an insertion force.

The method further includes wherein the differential resistances simulate forces encountered when injecting using an medicament-containing injection device comprising factors consisting of at least one of: injection angle, needle length, needle point, needle coating, lubrication of needle or injection site, needle depth into composite tissue, or a combination thereof.

In a further non-limiting embodiment, the method includes applying a force to the distal end of the injection simulation member, wherein as the injection simulation member is retracted, a resistance increases to simulate a deformation force until at least a first retracted position is reached, wherein upon reaching the first retracted position, the resistance decreases to simulate a puncture rebound force, and continuing to apply a force to the distal end of the injection simulation member, wherein following the decrease in resistance, a biasing member in the device housing causes an increase in resistance as the injection simulation member is further retracted to simulate an insertion force until at least a second retracted position is reached.

In still a further embodiment, an injection simulation device configured to simulate one or more forces applied to an injection device during an injection event is provided. The injection simulation device including a housing, an injection simulation member, the injection simulation member configured to be retracted from an extended position to a retracted position in response to a force on the injection simulation member, and a resistance mechanism, wherein the resistance mechanism provides one or more resistance values as the injection simulation member is retracted to simulate one or more forces applied during an injection event, wherein the resistance increases as the injection simulation member is retracted to simulate an insertion force according to: $F(x)=K*X^P$ wherein $F(x)$ is a force value at a point between the extended position and the retracted position, K is a resistance value comprising a resistance of the injection simulation device, X is a displacement value, and P is an exponential power value greater than zero. In an embodiment, the retracted position comprises a fully retracted position.

In one embodiment, as the P value increases, the force value increases exponentially. In a non-limiting embodiment, the P value may range between 0.5 and 4. In a non-limiting embodiment, the X value may range between 0.000001 mm and 250 mm.

In a further embodiment, the resistance mechanism of the injection simulation device includes a biasing member for providing a resistance on the retraction of the injection simulation member to simulate an insertion force as the force is applied to the injection simulation member to retract the injection simulation member. In one non-limiting embodiment, the biasing member may include a digressive spring. In a further, non-limiting embodiment, the digressive spring may include a Belleville spring, wherein the Belleville spring is compressed as the injection simulation member is retracted and a resistance on the retraction of the injection simulation member increases until the Belleville spring reaches a threshold compression level, wherein upon reaching the threshold compression level, the resistance on the injection simulation device decreases to simulate a force profile of the insertion force. In an embodiment, the biasing member may include a non-linear spring.

In another embodiment, the injection simulation device resistance mechanism may include a first engaging component and a second engaging component. The first engaging component may be associated with the device housing, such as in a non-limiting example, associated with an inner surface of a portion of the device housing, and the second engaging component may be associated with the injection simulation member. In one non-limiting embodiment, the second engaging component may be a protrusion on the injection simulation member, in another embodiment, the second engaging component may include a surface texture, or a particular material, such as a rubber material in a non-limiting example, on at least a portion of the second engaging component. The first and second engaging components are configured to move relative to one another as the injection simulation member is retracted into the device housing to provide a resistance to simulate an insertion force.

In a further non-limiting embodiment, the resistance mechanism may include a pneumatic component, wherein as the injection simulation member is retracted from an extended position upon an application of a force, an increase in air compression in the injection simulation housing occurs. The increase in air compression in the housing causes a resistance on the retraction of the injection simulation member to simulate the insertion force. An increase in air pressure occurring within the housing due to the retraction of the injection simulation member causes an increase in force, i.e., a pneumatic pressure build up to simulate an injection.

In still a further embodiment, an injection simulation device is provided having a housing and a retractable injection simulation member, said injection simulation member configured to simulate a needle of an injection device with a determined gauge (G) and which device is configured such that the injection simulation member retracts from an extended position to a retracted position under application of a force, (N), to simulate a insertion force (Force$_i$) according to the following formula: Force$_i$=2[C (−0.046(G)+1.83)], wherein the force value ranges between +/−1%-30% and every integer in between, and wherein C comprises a coefficient, said coefficient being a factor of the insertion force of the injection simulation device. The force value may range between +/−1%-20% and every integer in between. In another embodiment, the force values ranges +/−1%-10% and every integer in between. The insertion force (Force$_i$) includes the force required to retract the injection simulation member from an extended position to a retracted position. In one embodiment, the coefficient C value decreases when a longitudinal axis of the injection simulation member is generally perpendicular to a plane in which a surface comprising the injection site is disposed, and increases when an angle between the longitudinal axis of the injection simulation member and the plane in which the surface comprising the injection site decreases. In an embodiment, the retracted position includes a fully retracted position.

In one particular embodiment, the C value comprises 1.0 when the angle between the longitudinal axis of the injection simulation member and the plane of the surface comprising the injection site comprises 90 degrees. In another embodiment, the C value comprises 1.4 when the angle between the longitudinal axis of the injection simulation member and the plane of the surface comprising the injection site comprises 45 degrees. The table below includes non-limiting examples of data points obtained which include needle gauge (G) values, angle of injection (90 degrees) and a peak force range in Newtons, which includes a force of insertion of the needle to a fully inserted position, which is simulated with the injection simulation device embodiments provided herein, such that the peak force range corresponds to the Force$_i$, i.e., retraction of the injection simulation member from an extended to a retracted position.

SUMMARY

| Needle Gauge | Angle (Flat) (Degrees | Peak Force Range (Newtons) |
| --- | --- | --- |
| 18 (Regular) | 90 | 2.35-2.95 |
| 18 (Short) | 90 | .95-3.25 |
| 25 | 90 | 1.45-2.45 |
| 30 | 90 | .9-1.95 |

It is to be noted that the terms "first," "second," and the like as used herein do not denote any order, quantity, or importance, but rather are used to distinguish one element from another. The terms "a" and "an" do not denote a limitation of quantity, but rather denote the presence of at least one of the referenced item. It is to be noted that all ranges disclosed within this specification are inclusive and are independently combinable. The terminology used herein is for the purpose of describing particular embodiments only and is not intended to be limiting. As used herein, the singular forms "a," "an," and "the" are intended to include the plural forms as well, unless the context clearly indicates otherwise these terms do not denote a limitation of quantity, but rather denote the presence of at least one of the referenced item. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order, quantity or importance, but rather the terms first, second, etc., are used to distinguish one element from another.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. As a non-limiting example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 7.

It should be borne in mind that all patents, patent applications, patent publications, technical publications, scientific publications, and other references referenced herein are hereby incorporated by reference in this application in order to more fully describe the state of the art to which the present invention pertains.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the preceding definitions are provided.

While a number of embodiments of the present invention have been shown and described herein in the present context, such embodiments are provided by way of example only, and not of limitation. Numerous variations, changes and substitutions will occur to those of skill in the art without materially departing from the invention herein. For example, the present invention need not be limited to best mode disclosed herein, since other applications can equally benefit from the teachings of the present invention. Also, in the claims, any means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

The invention claimed is:

1. An injection simulation device comprising:
   a housing comprising a proximal end and a distal end;
   a plunger comprising a proximal end and a distal end and being slidable relative to the housing;
   a retractable injection simulation member at the distal end of the housing, the retractable injection simulation member being movable between an extended position and a retracted position;
   at least one first biasing member, wherein the at least one first biasing member is associated with the retractable injection simulation member, and directly or indirectly associated with the plunger;
   wherein a first force on a distal end of the retractable injection simulation member causes movement of the retractable injection simulation member from the extended position to the retracted position, to compress the at least one first biasing member, and simulate a tactility of an injection to a user; and
   wherein a second force on the proximal end of the plunger asserts a third force directly or indirectly on the at least one first biasing member to facilitate resetting the retractable injection simulation member to the extended position.

2. The injection simulation device of claim 1, further comprising an intervening component interfacing with the plunger and the retractable injection simulation member whereby the second force on the proximal end of the plunger causes the intervening component to impart the third force on the at least one first biasing member.

3. The injection simulation device of claim 2, wherein the intervening component comprises a second biasing member.

4. The injection simulation device of claim 1, wherein a release of the first force on the distal end of the retractable injection simulation member, optionally in combination with the second force on the proximal end of the plunger, allows the at least one first biasing member to expand, causing the retractable injection simulation member to extend.

5. The injection simulation device of claim 1, wherein the at least one first biasing member is directly associated with the plunger such that the plunger directly asserts the third force on the at least one first biasing member.

6. The injection simulation device of claim 1, wherein the at least one first biasing member is configured to provide a resistance simulating a deformation force of a needle, or an insertion force of a needle, or both, during an injection event upon applying the first force.

7. The injection simulation device of claim 1, wherein the retractable injection simulation member comprises a proximal end associated with the injection simulation device, and a distal end, wherein the distal end comprises an agitator having an agitator base portion associated with the distal end, an agitator tip, and an agitator body between the agitator base portion and the agitator tip.

8. The injection simulation device of claim 7, wherein the agitator body is between 1.0-3.0 mm in length.

9. The injection simulation device of claim 7, wherein the agitator body comprises a tip portion located 0.2-0.5 mm proximally from the agitator tip.

10. The injection simulation device of claim 7, wherein an area within a perimeter of a transverse plane along the agitator body ranges from [0.03-10 mm$^2$].

11. The injection simulation member of claim 7, wherein an area within a perimeter of a transverse plane of the agitator base portion is greater than an area within a perimeter of a subjacent transverse plane of the agitator body or an area within a perimeter of a transverse plane of the tip portion.

12. The injection simulation member of claim 9, wherein an area within a perimeter of a transverse plane of the agitator base portion is substantially equal to a surface area of a subjacent transverse plane of the agitator body or a transverse plane of the tip portion.

13. The injection simulation device of claim 9, wherein a surface area of a transverse plane of the tip portion ranges between 0.03-3.5 mm².

\* \* \* \* \*